(12) United States Patent
Salahieh et al.

(10) Patent No.: US 12,290,302 B2
(45) Date of Patent: May 6, 2025

(54) ENERGY DELIVERY DEVICE AND METHODS OF USE

(71) Applicant: Covidien LP, Mansfield, MA (US)

(72) Inventors: Amr Salahieh, Saratoga, CA (US);
Jonah Lepak, Saratoga, CA (US);
Emma Leung, Saratoga, CA (US);
John P. Claude, Saratoga, CA (US);
Tom Saul, Saratoga, CA (US)

(73) Assignee: Covidien LP, Mansfield, MA (US)

( * ) Notice: Subject to any disclaimer, the term of this patent is extended or adjusted under 35 U.S.C. 154(b) by 493 days.

(21) Appl. No.: 17/188,833

(22) Filed: Mar. 1, 2021

(65) Prior Publication Data

US 2021/0251681 A1 Aug. 19, 2021

Related U.S. Application Data

(63) Continuation of application No. 14/348,035, filed as application No. PCT/US2012/057967 on Sep. 28, 2012, now abandoned.
(Continued)

(51) Int. Cl.
*A61B 18/14* (2006.01)
*A61N 1/05* (2006.01)
(Continued)

(52) U.S. Cl.
CPC ............... *A61B 18/14* (2013.01); *A61N 1/05* (2013.01); *A61B 2018/00029* (2013.01);
(Continued)

(58) Field of Classification Search
CPC .. A61B 18/14; A61B 2018/00029; A61N 1/05
See application file for complete search history.

(56) References Cited

U.S. PATENT DOCUMENTS

| 4,547,193 A | 10/1985 | Rydell |
| 4,634,432 A | 1/1987 | Kocak |

(Continued)

FOREIGN PATENT DOCUMENTS

| CN | 1781161 A | 5/2006 |
| DE | 4104092 A1 | 8/1991 |

(Continued)

OTHER PUBLICATIONS

International Search Report and Written Opinion dated Apr. 10, 2013 in International Application No. PCT/US2012/057967.
(Continued)

*Primary Examiner* — Linda C Dvorak
*Assistant Examiner* — Ryan T Clark
(74) *Attorney, Agent, or Firm* — Shumaker & Sieffert, P.A.

(57) ABSTRACT

The present disclosure is directed to an expandable energy delivery assembly adapted to deliver electrical energy to tissue. The assembly includes an elongate device and an expandable portion. The expandable portion includes an inflatable element, a single helical electrode disposed on the inflatable element, and at least one irrigation aperture within the inflatable element. The inflatable element is secured to the elongate device and the single helical electrode makes between about 0.5 and about 1.5 revolutions around the inflatable element. The at least one irrigation aperture is adapted to allow fluid to flow from within the inflatable element to outside the inflatable element.

25 Claims, 10 Drawing Sheets

Related U.S. Application Data

(60) Provisional application No. 61/593,147, filed on Jan. 31, 2012, provisional application No. 61/541,765, filed on Sep. 30, 2011.

(51) Int. Cl.
  *A61B 18/00* (2006.01)
  *A61B 90/00* (2016.01)

(52) U.S. Cl.
  CPC ........... *A61B 2018/0022* (2013.01); *A61B 2018/00434* (2013.01); *A61B 2018/00577* (2013.01); *A61B 2018/00642* (2013.01); *A61B 2018/00708* (2013.01); *A61B 2018/00815* (2013.01); *A61B 2018/00821* (2013.01); *A61B 2018/1435* (2013.01); *A61B 2090/064* (2016.02); *A61B 2090/3966* (2016.02); *Y10T 29/49124* (2015.01)

(56) References Cited

U.S. PATENT DOCUMENTS

| | | |
|---|---|---|
| 4,726,382 A | 2/1988 | Boehmer et al. |
| 4,890,623 A | 1/1990 | Cook et al. |
| 4,968,306 A | 11/1990 | Huss et al. |
| 5,010,895 A | 4/1991 | Maurer et al. |
| 5,041,089 A | 8/1991 | Mueller et al. |
| 5,069,674 A | 12/1991 | Fearnot et al. |
| 5,180,376 A | 1/1993 | Fischell |
| 5,209,741 A | 5/1993 | Spaeth |
| 5,213,576 A | 5/1993 | Abiuso et al. |
| 5,228,442 A | 7/1993 | Imran |
| 5,277,201 A | 1/1994 | Stern |
| 5,309,910 A | 5/1994 | Edwards et al. |
| 5,311,866 A | 5/1994 | Kagan et al. |
| 5,343,860 A | 9/1994 | Metzger et al. |
| 5,391,200 A | 2/1995 | Kenknight et al. |
| 5,443,470 A | 8/1995 | Stern et al. |
| 5,515,848 A | 5/1996 | Corbett, III et al. |
| 5,524,338 A | 6/1996 | Martyniuk et al. |
| 5,540,679 A | 7/1996 | Fram et al. |
| 5,558,672 A | 9/1996 | Edwards et al. |
| 5,562,720 A | 10/1996 | Stern et al. |
| 5,569,241 A | 10/1996 | Edwards |
| 5,571,086 A | 11/1996 | Kaplan et al. |
| 5,571,088 A | 11/1996 | Lennox et al. |
| 5,573,520 A | 11/1996 | Schwartz et al. |
| 5,575,772 A | 11/1996 | Lennox |
| 5,575,788 A | 11/1996 | Baker et al. |
| 5,609,574 A | 3/1997 | Kaplan et al. |
| 5,626,564 A | 5/1997 | Zhan et al. |
| 5,630,837 A | 5/1997 | Crowley |
| 5,681,308 A | 10/1997 | Edwards et al. |
| 5,715,825 A | 2/1998 | Crowley |
| 5,718,701 A | 2/1998 | Shai et al. |
| 5,735,846 A | 4/1998 | Panescu et al. |
| 5,769,846 A | 6/1998 | Edwards et al. |
| 5,846,196 A | 12/1998 | Siekmeyer et al. |
| 5,888,577 A | 3/1999 | Griffin, III et al. |
| 5,902,251 A | 5/1999 | Vanhooydonk |
| 5,904,651 A | 5/1999 | Swanson et al. |
| 5,938,660 A | 8/1999 | Swartz et al. |
| 5,991,650 A | 11/1999 | Swanson et al. |
| 6,024,740 A | 2/2000 | Lesh et al. |
| 6,041,260 A | 3/2000 | Stern et al. |
| 6,052,607 A | 4/2000 | Edwards et al. |
| 6,163,716 A | 12/2000 | Edwards et al. |
| 6,163,726 A | 12/2000 | Wolf |
| 6,164,283 A | 12/2000 | Lesh |
| 6,190,382 B1 | 2/2001 | Ormsby et al. |
| 6,206,912 B1 | 3/2001 | Goldsteen et al. |
| 6,292,689 B1 | 9/2001 | Wallace et al. |
| 6,383,151 B1 * | 5/2002 | Diederich .......... A61B 18/1492 601/2 |
| 6,402,746 B1 | 6/2002 | Whayne et al. |
| 6,409,722 B1 * | 6/2002 | Hoey ............ A61B 18/18 606/41 |
| 6,416,511 B1 | 7/2002 | Lesh et al. |
| 6,460,545 B2 | 10/2002 | Kordis |
| 6,502,576 B1 | 1/2003 | Lesh |
| 6,551,309 B1 | 4/2003 | LePivert |
| 6,558,378 B2 | 5/2003 | Sherman et al. |
| 6,572,609 B1 | 6/2003 | Farr et al. |
| 6,572,612 B2 | 6/2003 | Stewart et al. |
| 6,595,989 B1 | 7/2003 | Schaer |
| 6,635,054 B2 | 10/2003 | Fjield et al. |
| 6,641,553 B1 | 11/2003 | Chee et al. |
| 6,743,226 B2 | 6/2004 | Cosman et al. |
| 6,758,847 B2 | 7/2004 | Maguire |
| 6,808,524 B2 | 10/2004 | Lopath et al. |
| 6,814,730 B2 | 11/2004 | Li |
| 6,872,183 B2 | 3/2005 | Sampson et al. |
| 6,872,205 B2 | 3/2005 | Lesh et al. |
| 6,872,206 B2 | 3/2005 | Edwards et al. |
| 6,875,193 B1 | 4/2005 | Bonnette et al. |
| 6,911,027 B1 | 6/2005 | Edwards et al. |
| 6,978,174 B2 | 12/2005 | Gelfand et al. |
| 7,004,923 B2 | 2/2006 | Deniega et al. |
| 7,048,733 B2 | 5/2006 | Hartley et al. |
| 7,063,670 B2 | 6/2006 | Sampson et al. |
| 7,115,122 B1 | 10/2006 | Swanson et al. |
| 7,137,395 B2 | 11/2006 | Fried et al. |
| 7,137,977 B2 | 11/2006 | Brucker et al. |
| 7,138,170 B2 | 11/2006 | Bourdelais et al. |
| 7,162,303 B2 | 1/2007 | Levin et al. |
| 7,163,534 B2 | 1/2007 | Brucker et al. |
| 7,169,142 B2 | 1/2007 | Brucker et al. |
| 7,207,984 B2 | 4/2007 | Farr et al. |
| 7,226,448 B2 | 6/2007 | Bertolero et al. |
| 7,232,437 B2 | 6/2007 | Berman et al. |
| 7,238,179 B2 | 7/2007 | Brucker et al. |
| 7,238,180 B2 | 7/2007 | Mester et al. |
| 7,241,295 B2 | 7/2007 | Maguire |
| 7,267,674 B2 | 9/2007 | Brucker et al. |
| 7,286,866 B2 | 10/2007 | Okerlund et al. |
| 7,310,150 B2 | 12/2007 | Guillermo et al. |
| 7,320,677 B2 | 1/2008 | Brouillette |
| 7,326,201 B2 | 2/2008 | Fjield et al. |
| 7,338,485 B2 | 3/2008 | Brucker et al. |
| 7,344,535 B2 | 3/2008 | Stern et al. |
| 7,346,381 B2 | 3/2008 | Okerlund et al. |
| 7,357,796 B2 | 4/2008 | Farr et al. |
| 7,365,859 B2 | 4/2008 | Yun et al. |
| 7,366,376 B2 | 4/2008 | Shishkov et al. |
| 7,382,949 B2 | 6/2008 | Bouma et al. |
| 7,396,355 B2 | 7/2008 | Goldman et al. |
| 7,406,970 B2 | 8/2008 | Zikorus et al. |
| 7,413,568 B2 | 8/2008 | Swanson et al. |
| 7,418,169 B2 | 8/2008 | Tearney et al. |
| 7,429,260 B2 | 9/2008 | Underwood et al. |
| 7,429,261 B2 | 9/2008 | Kunis et al. |
| 7,445,618 B2 | 11/2008 | Eggers et al. |
| 7,447,408 B2 | 11/2008 | Bouma et al. |
| 7,452,358 B2 | 11/2008 | Stern et al. |
| 7,468,062 B2 | 12/2008 | Oral et al. |
| 7,473,251 B2 | 1/2009 | Knowlton et al. |
| 7,481,809 B2 | 1/2009 | Stern et al. |
| 7,489,969 B2 | 2/2009 | Knudson et al. |
| 7,507,236 B2 | 3/2009 | Eggers et al. |
| 7,510,555 B2 | 3/2009 | Kanzius |
| 7,519,096 B2 | 4/2009 | Bouma et al. |
| 7,529,393 B2 | 5/2009 | Peszynski et al. |
| 7,538,859 B2 | 5/2009 | Tearney et al. |
| 7,617,005 B2 | 11/2009 | Demarais et al. |
| 7,669,309 B2 | 3/2010 | Johnson et al. |
| 7,756,583 B2 | 7/2010 | Demarais et al. |
| 7,853,333 B2 | 12/2010 | Demarais |
| 7,937,143 B2 | 5/2011 | Demarais et al. |
| 8,708,953 B2 | 4/2014 | Salahieh et al. |
| 8,800,551 B2 | 8/2014 | Tang |
| 9,610,006 B2 | 4/2017 | Salahieh et al. |
| 2002/0002384 A1 | 1/2002 | Gilson et al. |

(56) References Cited

U.S. PATENT DOCUMENTS

| | | | |
|---|---|---|---|
| 2002/0062119 A1* | 5/2002 | Zadno-Azizi | A61F 2/01 604/509 |
| 2002/0095147 A1 | 7/2002 | Shadduck | |
| 2003/0093069 A1 | 5/2003 | Panescu et al. | |
| 2003/0097121 A1 | 5/2003 | Jolly et al. | |
| 2003/0195501 A1 | 10/2003 | Sherman et al. | |
| 2003/0236443 A1 | 12/2003 | Cespedes et al. | |
| 2004/0243118 A1 | 12/2004 | Ayers et al. | |
| 2005/0171525 A1* | 8/2005 | Rioux | A61B 18/1492 606/41 |
| 2005/0203597 A1 | 9/2005 | Yamazaki et al. | |
| 2005/0251131 A1 | 11/2005 | Lesh | |
| 2005/0288730 A1 | 12/2005 | Deem et al. | |
| 2006/0041277 A1 | 2/2006 | Deem et al. | |
| 2006/0206150 A1 | 9/2006 | Demarais et al. | |
| 2006/0210605 A1 | 9/2006 | Chang et al. | |
| 2006/0212078 A1 | 9/2006 | Demarais et al. | |
| 2006/0247701 A1 | 11/2006 | Zacouto | |
| 2006/0265014 A1 | 11/2006 | Demarais et al. | |
| 2006/0265015 A1 | 11/2006 | Demarais et al. | |
| 2006/0271111 A1 | 11/2006 | Demarais et al. | |
| 2006/0276852 A1 | 12/2006 | Demarais et al. | |
| 2007/0078507 A1 | 4/2007 | Zacouto | |
| 2007/0112422 A1 | 5/2007 | Dehdashtian | |
| 2007/0118094 A1 | 5/2007 | Bingham et al. | |
| 2007/0129720 A1 | 6/2007 | Demarais et al. | |
| 2007/0129760 A1 | 6/2007 | Demarais et al. | |
| 2007/0135875 A1 | 6/2007 | Demarais et al. | |
| 2007/0213671 A1 | 9/2007 | Hiatt | |
| 2007/0225634 A1 | 9/2007 | Ferren et al. | |
| 2007/0244501 A1 | 10/2007 | Horn et al. | |
| 2008/0097427 A1 | 4/2008 | Stern et al. | |
| 2008/0161802 A1 | 7/2008 | Swanson et al. | |
| 2008/0188912 A1 | 8/2008 | Stone et al. | |
| 2008/0205481 A1 | 8/2008 | Faries et al. | |
| 2008/0275445 A1 | 11/2008 | Kelly et al. | |
| 2008/0281312 A1 | 11/2008 | Werneth et al. | |
| 2008/0281322 A1 | 11/2008 | Sherman et al. | |
| 2008/0296152 A1 | 12/2008 | Voss | |
| 2009/0024195 A1 | 1/2009 | Rezai et al. | |
| 2009/0149846 A1* | 6/2009 | Hoey | A61M 25/10 606/27 |
| 2009/0227885 A1 | 9/2009 | Lowery et al. | |
| 2009/0240249 A1 | 9/2009 | Chan et al. | |
| 2009/0254142 A1 | 10/2009 | Edwards et al. | |
| 2009/0299355 A1* | 12/2009 | Bencini | A61B 18/02 606/21 |
| 2009/0312754 A1 | 12/2009 | Lenihan et al. | |
| 2010/0004650 A1 | 1/2010 | Ormsby et al. | |
| 2010/0262140 A1 | 10/2010 | Watson et al. | |
| 2010/0331776 A1 | 12/2010 | Salahieh et al. | |
| 2011/0034790 A1 | 2/2011 | Mourlas et al. | |
| 2011/0046600 A1 | 2/2011 | Crank | |
| 2011/0077579 A1 | 3/2011 | Harrison et al. | |
| 2011/0257622 A1 | 10/2011 | Salahieh et al. | |
| 2011/0264086 A1* | 10/2011 | Ingle | A61B 18/1492 606/33 |
| 2012/0116438 A1 | 5/2012 | Salahieh et al. | |
| 2013/0138082 A1 | 5/2013 | Salahieh et al. | |
| 2013/0289549 A1* | 10/2013 | Nash | A61B 18/02 606/21 |
| 2014/0107623 A1 | 4/2014 | Salahieh et al. | |
| 2015/0066013 A1 | 3/2015 | Salahieh et al. | |
| 2021/0162114 A1 | 6/2021 | Salahieh et al. | |

FOREIGN PATENT DOCUMENTS

| | | |
|---|---|---|
| DE | 4104902 A1 | 8/1992 |
| EP | 0637943 A1 | 2/1995 |
| EP | 0693955 A1 | 1/1996 |
| EP | 0723467 A1 | 7/1996 |
| EP | 1382366 A1 | 1/2004 |
| EP | 2335757 A2 | 6/2011 |
| JP | 2000504242 A | 4/2000 |
| WO | 9725917 A1 | 7/1997 |
| WO | 99/00060 A1 | 1/1999 |
| WO | 00/66014 A1 | 11/2000 |
| WO | 2009067695 A1 | 5/2009 |
| WO | 2009/132137 A1 | 10/2009 |

OTHER PUBLICATIONS

Drafts, "Acoustic wave technology sensors", Sensors Weekley, Oct. 1, 2000, 10 pp.

U.S. Appl. No. 13/830,624, filed Mar. 14, 2013, naming inventors Salahieh et al.

Office Action from U.S. Appl. No. 14/391,641, dated Nov. 5, 2021, 11 pp.

* cited by examiner

ENERGY DELIVERY DEVICE AND METHODS OF USE

CROSS REFERENCE TO RELATED APPLICATIONS

The present application is a continuation of U.S. patent application Ser. No. 14/348,035, filed Mar. 27, 2014, which is a national stage entry under 35 U.S.C. 371 of International Patent Application No. PCT/US2012/057967, filed Sep. 28, 2012, which claims the benefit of priority to U.S. Provisional Application Ser. No. 61/541,765, filed on Sep. 30, 2011, and to U.S. Provisional Application Ser. No. 61/593,147, filed on Jan. 31, 2012, with the entire contents of each of these applications incorporated herein by reference. This application is also related to and incorporates by reference herein the complete disclosures of the following patent applications: U.S. Provisional Pat. App. No. 61/113,228, filed Dec. 11, 2008; U.S. Provisional Pat. App. No. 61/160,204, filed Mar. 13, 2009; U.S. Provisional Pat. App. No. 61/179,654, filed May 19, 2009; U.S. Pat. App. Pub. No. 2010/0204560, filed Nov. 11, 2009; U.S. Provisional Pat. App. No. 61/334,154, filed May 12, 2010; and U.S. patent application Ser. No. 13/106,658, filed May 12, 2011.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present disclosure relates generally to medical devices and methods and more particularly to devices and methods for applying radiofrequency energy to tissue.

BACKGROUND

Some medical treatment procedures involve the disruption of a region of tissue. For example, medical treatment procedures include the delivery of energy to disrupt a region of tissue. Radiofrequency ("RF") energy devices are an example of devices that can be used to perform such medical treatments.

Some RF energy devices have a single RF energy element or a plurality of discrete RF energy elements that have to be repeatedly moved within the subject in order to apply sufficient RF energy to the entire region of the tissue. Such RF energy devices may need to be moved within a patient during a given procedure, which can increase the complexity, time, and energy required to perform a given procedure.

SUMMARY

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

As used herein, the terms proximal and distal refer to a direction or a position along a longitudinal axis of a catheter or medical instrument. The term "proximal" refers to the end of the catheter or medical instrument closer to the operator, while the term "distal" refers to the end of the catheter or medical instrument closer to the patient. For example, a first point is proximal to a second point if it is closer to the operator end of the catheter or medical instrument than the second point. The measurement term "French", abbreviated Fr or F, is defined as three times the diameter of a device as measured in mm. Thus, a 3 mm diameter catheter is 9 French in diameter. The term "operator" refers to any medical professional (i.e., doctor, surgeon, nurse, or the like) performing a medical procedure involving the use of aspects of the present disclosure described herein.

In an aspect of the present disclosure, an expandable energy delivery assembly adapted to deliver electrical energy to tissue is provided. The assembly includes an elongate device and an expandable portion. The expandable portion includes an inflatable element, a single helical electrode disposed on the inflatable element, and at least one irrigation aperture within the inflatable element. The inflatable element is secured to the elongate device and the single helical electrode makes between about 0.5 and about 1.5 revolutions around the inflatable element. The at least one irrigation aperture is adapted to allow fluid to flow from within the inflatable element to outside the inflatable element.

The single helical electrode may make between about 1 and about 1.25 revolutions around the inflatable element.

A conductive material may be disposed on the elongate device proximal to the expandable portion to electrically couple the single helical electrode to an electrical energy source, wherein the conductive material is disposed on substantially the entire elongate device proximal to the expandable portion. An insulation material may be disposed on substantially all of the conductive material on the elongate device.

The conductive material and the single helical electrode may form a unitary conductive material without an electrical junction. The conductive material and the helical electrode may be an elastomeric ink.

The expandable portion may include a proximal transition section covered with a conductive material that electrically couples the helical electrode and the conductive material on the elongate device. An insulation material may be disposed on the conductive material on the transition shaped section.

The inflatable element is a balloon with a substantially cylindrical section, where the single helical electrode is disposed on the substantially cylindrical section. Additionally or alternatively, the at least one irrigation aperture is in the inflatable element, in the helical electrode, and/or adjacent the helical electrode.

In certain embodiments, the elongate device includes an irrigation lumen therein and an irrigation port therein. The irrigation port can be disposed within the inflatable element and can provide fluid communication between the irrigation lumen and the interior of the inflatable element.

In another aspect of the present disclosure, an expandable energy delivery assembly adapted to deliver energy to tissue is provided. The assembly includes an elongate device and an expandable element secured thereto. The assembly also includes a unitary conductive material disposed on substantially all of the elongate device proximal to the expandable element and on a portion of the expandable element. The unitary conductor being void of an electrical junction.

The expandable element may be an inflatable balloon. In some embodiments, the conductive material on the expandable element forms a single helix. The expandable element can include a transition portion with the conductive material also being disposed on the transition portion. An insulation material may be disposed over substantially all of the conductive material on the elongate device proximal to the expandable element. The transition portion may include a conically-shaped portion.

In yet another aspect of the present disclosure, an expandable energy delivery assembly adapted to deliver energy to tissue is provided that includes an elongate device comprising an irrigation lumen therethrough and an irrigation port proximal to a distal end of the elongate device. An inflatable element is secured to the elongate device such that the irrigation port is disposed within a fluid chamber defined by the inflatable element. An electrode is disposed on the inflatable element and at least one irrigation aperture is provided and adapted to allow fluid to pass from within the fluid chamber to outside the inflatable element. The irrigation aperture is sized to maintain a pressure within the inflatable element between about 0.5 atm and about 4 atm when a substantially constant irrigation flow rate is between about 5 mL/min and about 15 mL/min.

The assembly may also include a temperature sensor adapted to measure fluid temperature and may further include an energy source and a controller, the controller being adapted to automatically turn off the energy source if a sensed fluid temperature is above a threshold limit. The temperature sensor can be disposed within the inflatable element.

In some embodiments, the assembly includes a flow rate sensor adapted to sense fluid flow rate and may further include an energy source and a controller, the controller being adapted to automatically turn off the energy source if a sensed flow rate falls below a minimum value.

The assembly may include a pressure sensor adapted to sense fluid pressure and may further include an energy source and a controller, the controller being adapted to automatically turn off the energy source if a sensed pressure falls below a minimum value.

In yet another aspect of the present disclosure, a method of manufacturing an expandable energy delivery assembly adapted to deliver energy to tissue is provided. The method includes: providing an inflatable element secured to an elongate device; inflating the inflatable element; and depositing a conductive material on an exterior surface of the inflatable element to form a single helical electrode making between about 0.5 and about 1.5 revolutions around the inflatable element.

Depositing may include vapor deposition, electroplating, electroless plating, pad printing, spraying, or ink jet. A mask may be applied to the inflatable element before the depositing step. In some embodiments, the depositing step includes depositing the conductive material on substantially all of the elongate device proximal to the inflatable device and on the inflatable element, forming a unitary conductor. The depositing step may also include depositing the conductive material on a conical section of the inflatable element.

In some embodiments, the mask is removed, a second mask is applied over the helical electrode, and an insulation material is deposited over substantially all of the elongate device proximal to the inflatable element. Depositing the insulation material can include depositing the insulation material over a transition section of the inflatable element. Additionally or alternatively, applying the second mask can include applying the second mask over an entire intermediate section of the inflatable element.

In yet another aspect of the present disclosure, a method of manufacturing an expandable energy delivery assembly adapted to deliver energy to tissue is provided that includes: providing an inflatable element secured to an elongate device; inflating the inflatable element; and depositing a conductive material on the elongate device and a portion of the inflatable element in a single depositing step to faun a unitary conductor without an electrical junction.

The depositing step may include depositing the conductive material on substantially the entire elongate device proximal to the inflatable element Additionally or alternatively, depositing may include depositing the conductive material in a helical pattern on the inflatable element.

A mask may be applied over the inflatable element. In certain embodiments, the depositing step also includes depositing the conductive material over a transition section of the inflatable element.

An insulation layer is deposited over the conductive material on the elongate device.

The depositing step may include depositing an elastomeric conductive material on the elongate device and a portion of the inflatable element in a single depositing step to form an elastomeric unitary conductor.

In some embodiments, depositing the conductive material includes depositing the conductive material using vapor deposition, electroplating, electroless plating, pad printing and spraying, or ink jet.

In yet another aspect of the present disclosure, a method of providing an irrigation fluid to an inflatable medical device includes: providing an elongate device with an inflatable element secured thereto, the inflatable element defining a fluid chamber and comprising at least one irrigation aperture therein to allow a fluid to flow through the inflatable element, the elongate device comprising an irrigation lumen extending therethrough that provides fluid communication to the inflatable chamber; continuously flowing the fluid at a substantially constant flow rate between about 5 mL/min and about 15 mL/min from a fluid source and into the irrigation lumen while allowing fluid to flow out of the fluid chamber through the at least one irrigation aperture; and maintaining a fluid pressure within the inflatable element between about 0.5 atm and about 4 atm.

In yet another aspect of the present disclosure, a method of providing an irrigation fluid to an inflatable medical device includes: providing an elongate device with an inflatable element secured thereto, the inflatable element defining a fluid chamber and comprising at least one irrigation aperture therein to allow a fluid to flow through the inflatable element, the elongate device comprising an irrigation lumen extending therethrough that provides fluid communication to the inflatable chamber; and maintaining a substantially constant pressure between about 0.5 atm and about 4 atm within the inflatable element sufficient to maintain a flow rate of between about 5 mL/min and about 15 mL/min through the inflatable element and out of at least one irrigation aperture In some embodiments, these methods include delivering RF energy to tissue via an energy element disposed on the inflatable element. Additionally or alternatively, a temperature of the fluid may be sensed such that, for example, the delivery of RF energy can be stopped if the sensed temperature is above a threshold temperature. The delivery of RF energy may be stopped if the pressure within the inflatable element falls outside of a control range and/or if the flow through the inflatable element falls outside of a control range. The RF energy may be delivered through a unitary conductor comprising an electrode that may be, for example, a helically-configured electrode.

In certain embodiments, these methods include endovascularly disposing the inflatable element in a renal artery, applying RF energy through an electrode on the inflatable element to renal nerves to disrupt transmission of neural signals along the renal nerves to treat hypertension.

In yet another aspect of the present disclosure, a method of delivering RF energy to tissue includes: providing an elongate device with an inflatable element secured thereto, the inflatable element defining a fluid chamber and comprising at least one irrigation aperture therein to allow the fluid to flow through the inflatable element, the elongate device comprising an irrigation lumen extending therethrough that provides fluid communication to the inflatable chamber from a fluid source; continuously flowing a fluid at a substantially constant flow rate from the fluid source; sensing a temperature of the fluid; automatically stopping the delivery of RF energy to an electrode on the inflatable element if the sensed fluid temperature is above a threshold temperature.

Sensing a temperature of the fluid may include sensing a temperature of the fluid within the fluid chamber. Delivery of RF energy to an electrode on the inflatable element can be automatically stopped if the sensed fluid temperature is above about 60 degrees C.

In some embodiments, the method further includes endovascularly positioning the inflatable element within a renal artery, and RF energy is applied through the electrode on the inflatable element to renal nerves to disrupt transmission of neural signals along the renal nerves to treat hypertension. The RF energy may be delivered through a unitary conductor including an electrode that may be, for example, a helically-configured electrode.

In yet another aspect of the present disclosure, a method of treating hypertension is provided that includes: delivering RF energy from a helically-configured electrode disposed on an inflated element within a renal artery into a renal nerve to disrupt renal nerve transmission to treat hypertension; and substantially continuously flowing fluid through the inflated element to cool tissue adjacent the helically-configured electrode.

In yet another aspect of the present disclosure, a method of treating hypertension is provided that includes: positioning a unitary conductor comprising a helically-configured electrode disposed on an inflated element within a renal artery; delivering RF energy from the electrode and into a renal nerve to disrupt renal nerve transmission to treat hypertension; and flowing fluid through the inflated element to cool tissue adjacent the helically-configured electrode.

In yet another aspect of the present disclosure, an RF delivery device adapted to treat hypertension includes an expandable element secured to an elongate device and a unitary conductor disposed on a portion of the elongate device and a portion of the inflatable element. An insulation material is disposed on a portion of the unitary conductor, thereby forming a helically-configured electrode disposed on the expandable element. The expandable element includes a plurality of apertures therein.

In yet another aspect of the present disclosure, an expandable energy delivery assembly adapted to deliver electrical energy to tissue includes an elongate device and an expandable portion. The expandable portion includes an inflatable element, a first helical electrode disposed on the inflatable element, a second helical electrode disposed on the inflatable element and at least one irrigation aperture within the inflatable element. The inflatable element is secured to the elongate device, the first helical electrode makes between about 0.5 and about 1.5 revolutions around the inflatable element, the second helical electrode makes between about 0.5 and about 1.5 revolutions around the inflatable element, and the at least one irrigation aperture allows fluid to flow from within the inflatable element to outside the inflatable element.

In certain embodiments, the first helical electrode and the second helical electrode may be configured to operate in a bipolar mode or the first helical electrode or the second helical electrode may be configured to operate in a monopolar mode.

DETAILED DESCRIPTION

Figure 1A:
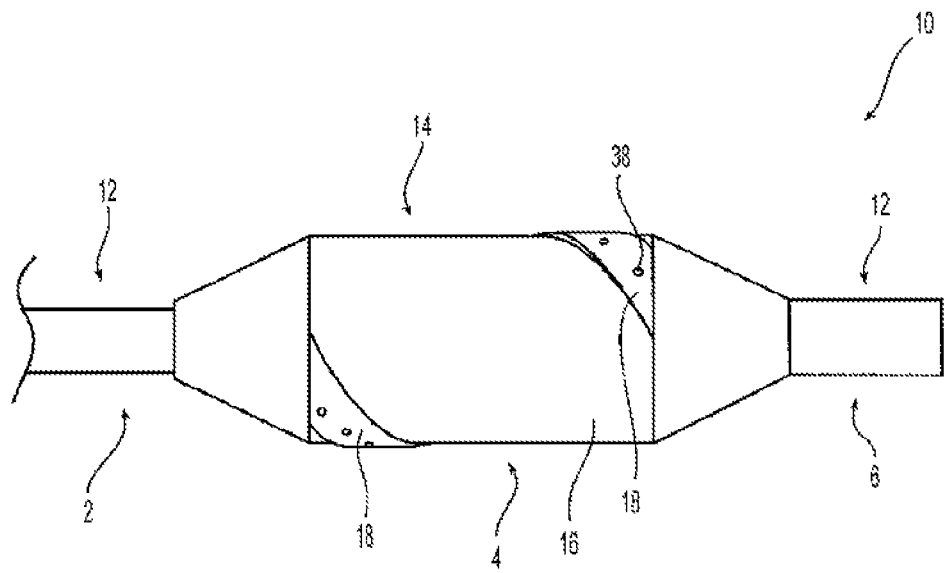
FIGS. 1A, 1B, and 2 illustrate a portion of an energy delivery device comprising a helical electrode on an expandable element according to an embodiment of the present disclosure.

Particular embodiments of the present disclosure are described hereinbelow with reference to the accompanying drawings; however, the disclosed embodiments are merely examples of the disclosure and may be embodied in various forms. Like reference numerals may refer to similar or identical elements throughout the description of the figures.

One aspect of the disclosure is a RF delivery device that is adapted to deliver RF energy to tissue. FIG. 1A illustrates a side view of a distal region of RF delivery device 10. Device 10 has proximal region 2, intermediate region 4, and distal region 6. Device 10 includes an elongate portion 12 and expandable portion 14 (shown in an expanded configuration) disposed on a distal region of elongate portion 12. Expandable portion 14 includes inflatable element 16 on which conductive material 18 is disposed.

Figure 1B:
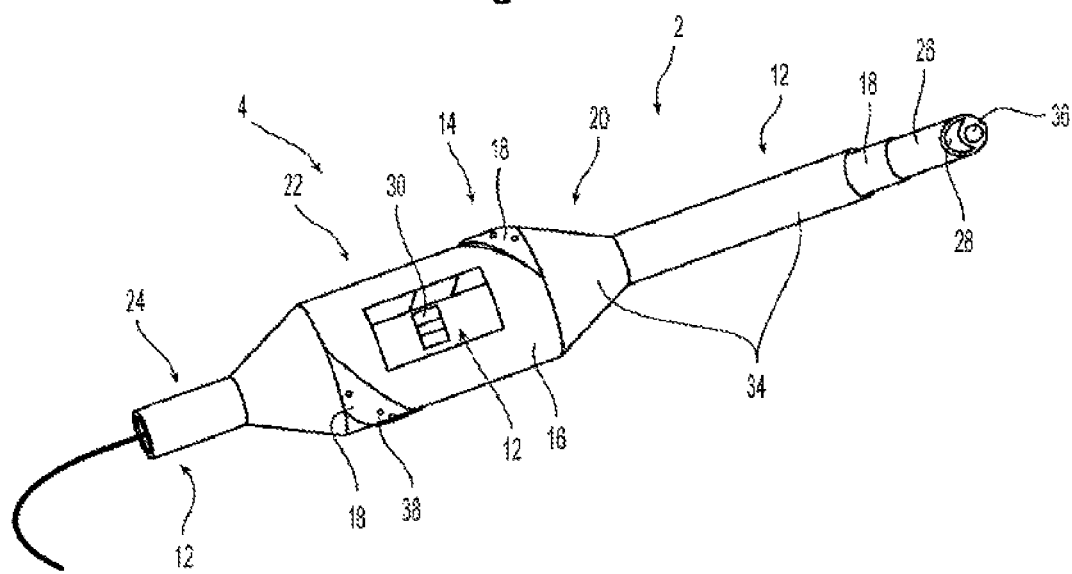

FIG. 1B illustrates a perspective view of the portion of the device shown in FIG. 1A, with a rectangular section of inflatable element 16 removed to illustrate elongate portion 12 disposed inside inflatable element 16.

Figure 2:
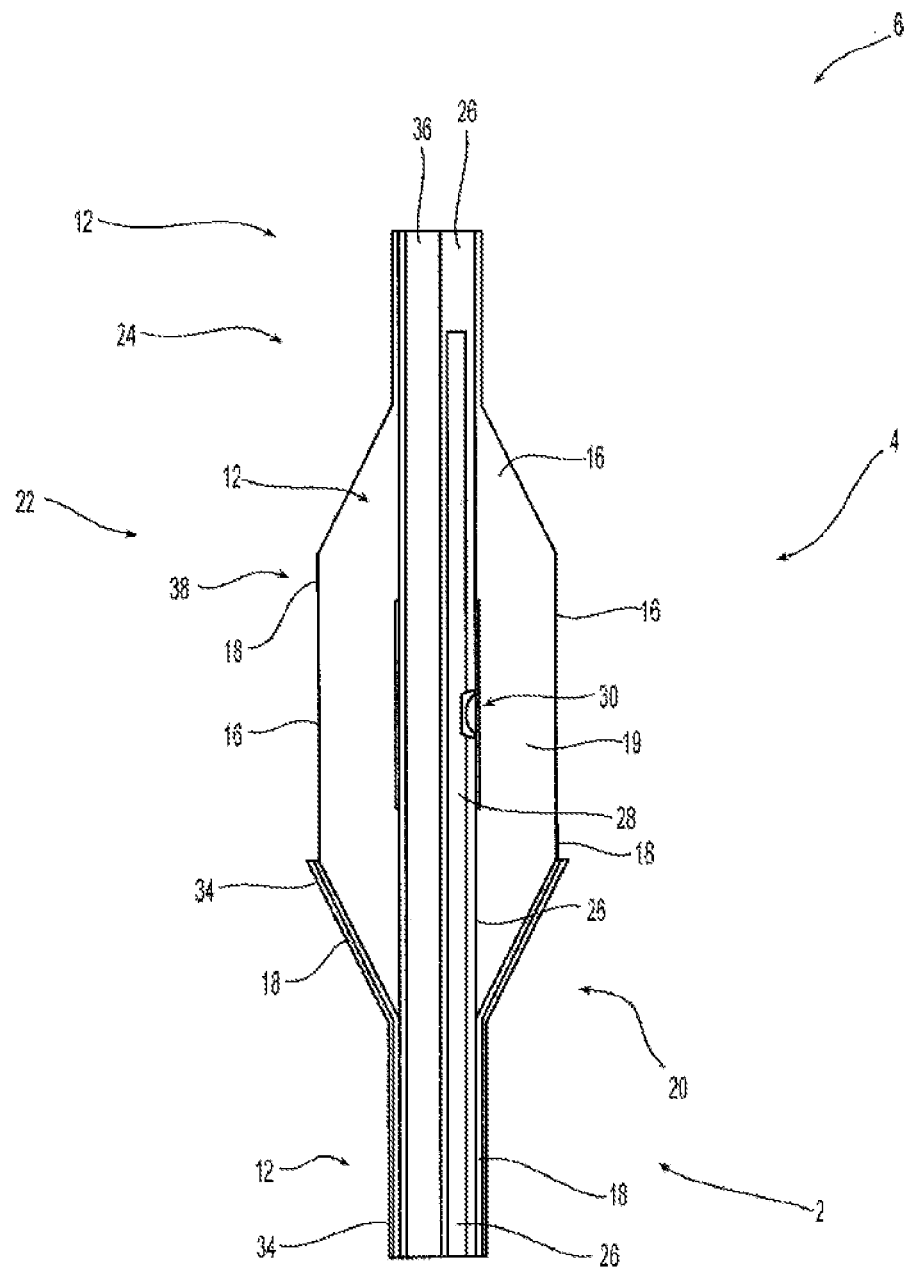

FIG. 2 shows a sectional view of the portion of the device shown in FIG. 1A. Expandable portion 14 includes a proximal transition section 20, intermediate section 22, and distal transition section 24. Proximal transition section 20 and distal transition section 24 are shown with conical configurations extending towards elongate portion 12 but are not limited to this configuration. Intermediate section 22 is substantially cylindrically-shaped when inflatable element 16 is in the expanded configuration shown in FIGS. 1A, 1B, and 2. The proximal end of inflatable element 16 and the distal end of inflatable element 16 are secured to catheter 26, which is part of elongate portion 12.

Conductive material 18 is disposed on catheter 26 proximal to the expandable portion 14, and it is also disposed on the cylindrical section of inflatable element 16 in a helical pattern forming a helical electrode 19 as shown. In proximal region 2 and in proximal section 20 of the expandable portion, insulation material 34 is disposed on the layer of conductive material 18. In the cylindrical intermediate section 22 of expandable portion 14, insulation material 34 is not disposed on the helical electrode, allowing energy to be delivered to tissue through conductive material 18. In the proximal region 2 of the device, and in proximal section 20 of expandable portion 14, conductive material 18 is covered with a layer of insulation, and thus energy is not applied to tissue in those areas. The conductive material that is not covered by dielectric material on the distal portion of the system is considered an electrode. The conductive material and the electrode are in this embodiment the same material.

The conductive material 18 is disposed on substantially the entire catheter 26 in proximal region 2 of the device. "Substantially the entire," or "substantially all," or derivatives thereof as used herein include the entire surface of catheter 26, but also includes most of the surface of the catheter. For example, if a few inches of the proximal end of catheter 26 are not covered with conductive material, conductive material is still considered to be disposed on substantially all of the catheter. The conductive material 18 and insulation material 34 extend 360 degrees around the catheter shaft, as opposed to only covering discrete lateral sections of the catheter. Alternatively, in some embodiments the conductor covers only a portion of the lateral surface of the catheter shaft. The conductive material and insulation material may cover the entirety or only a portion of the proximal transition section of the expandable portion. The insulation will typically cover the entirety of the conductive material in this region. The conductive material and insulation material could, however, also be disposed on the distal section 24 of expandable portion 14.

In some embodiments the helical electrode makes about 0.5 revolutions to about 1.5 revolutions around the inflatable element. The number of revolutions is measured over the length of the helical electrode. The electrode may extend from the proximal transition section to the distal transition section (as shown in FIG. 2), but the electrode may extend over any section of the inflatable element. For example, the proximal end of the electrode may be disposed distal to the proximal transition section, and the distal end of the electrode may be proximal to the distal transition section.

One revolution traverses 360 degrees around the longitudinal axis of the expandable element. One revolution of the electrode, along an end-view of inflatable device, forms a circle, although depending on the cross sectional shape of the expandable element, the electrode can form any variety of shapes in an end-view. An electrode making 0.5 revolutions therefore traverses one half of 360 degrees, or 180 degrees. An electrode making 0.5 revolutions has distal and proximal ends that are on opposite sides of the balloon. In an end-view of the inflatable element with a circular cross section, an electrode making 0.5 revolutions has a semicircular, or C, shape.

The proximal end of the electrode can be disposed anywhere on the expandable element and the distal end of the electrode can be anywhere on the expandable element, as long as the proximal end is proximal to the distal end. In some embodiments, the proximal end of the electrode is at the boundary between the proximal transition section and the cylindrical intermediate section of the expandable element, and the distal end of the electrode is at the boundary between the distal transition section and the cylindrical intermediate section. In other embodiments the proximal end of the electrode is disposed distal to the boundary between the proximal intermediate section and the cylindrical intermediate section of the expandable element, and the distal end is proximal to the boundary between the distal transition section and the central intermediate section of the expandable element. In these other embodiments the electrode is considered to extend along a subset of the length of the central intermediate section of the expandable element. In the embodiment shown in FIG. 1B, the electrode makes about 1 revolution around the inflatable element. In some embodiments the electrode makes about 0.5 revolutions around the inflatable element. In some embodiments the electrode makes about 0.75 revolutions around the inflatable element. In some embodiments the electrode makes about 1 revolution around the inflatable element. In some embodiments the electrode makes about 1.25 revolutions around the inflatable element. In some embodiments the electrode makes about 1.5 revolutions around the inflatable element.

The device is adapted to be coupled to an RF generator, which supplies RF current through the conductive material 18 on catheter 26 and inflatable element 16. In this manner RF current can be delivered to the desired tissue. Energy is thus applied to tissue in the configuration of the conductive material on the intermediate section 22 of the expandable portion 14, which in this embodiment is a helical, or spiral, configuration.

Figure 3A:
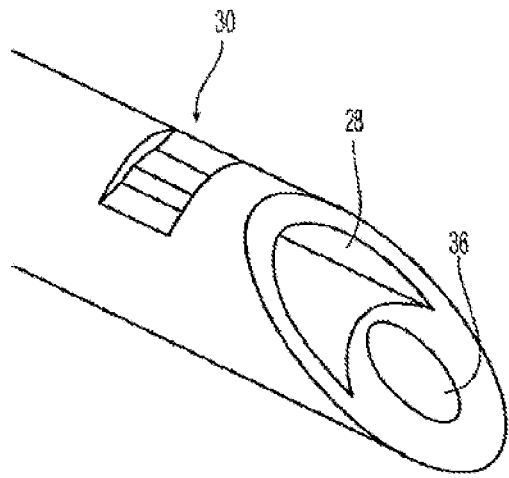
FIGS. 3A and 3B show a portion of an elongate device according to an embodiment of the present disclosure.
Figure 3B:
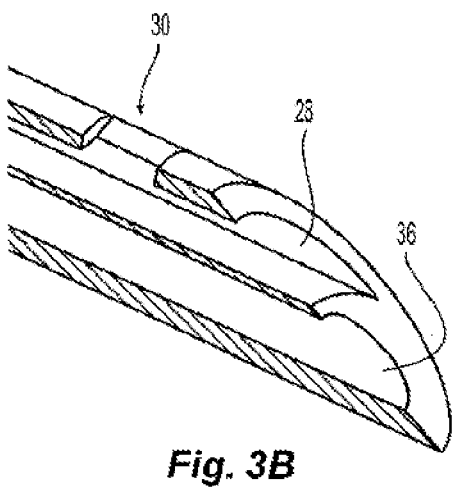

Within the expandable portion, catheter 26 is not covered with conductive material or insulation material. Catheter 26 includes guide element lumen 36 and inflation lumen 28, also referred to herein as irrigation lumen, extending therethrough. Guide element lumen 36 extends from the proximal end of the device (not shown) to the distal end. Irrigation lumen 28 extends from the proximal end of catheter 26 (not shown) to a location within inflatable element 16. Irrigation port 30 is located inside inflatable element 16 and is in between proximal and distal ends of irrigation lumen 28. Irrigation lumen 28 and irrigation port 30 provide for fluid communication between the irrigation lumen and the interior of inflatable element 16. FIGS. 3A and 3B illustrate additional views of guide element lumen 36, irrigation lumen 28, and irrigation port 30. In some embodiments catheter 26 ranges in size from 2 to 8 French, and in some embodiments is 4 Fr. In some embodiments the guide wire lumen is between 1 and 4 Fr and in some embodiments is 2.5 Fr.

Expandable portion 14 includes one or more irrigation apertures 38 to allow irrigation fluid to pass from inside inflatable element 16 to outside inflatable element 16. The irrigation apertures can be formed only in the electrode section of expandable portion 14 (see, for example, FIG. 1A), only in the non-electrode section of inflatable portion 14, or in both the electrode section and in the non-electrode section. The irrigation fluid is adapted to cool the conductive material 18 and/or tissue. The apertures allow for fluid to flow out of the balloon, allowing either a continuous or non-continuous supply of fluid from a fluid reservoir, through the lumen, and into the balloon. The irrigation fluid is in some embodiments cooled prior to delivery.

Figure 4:
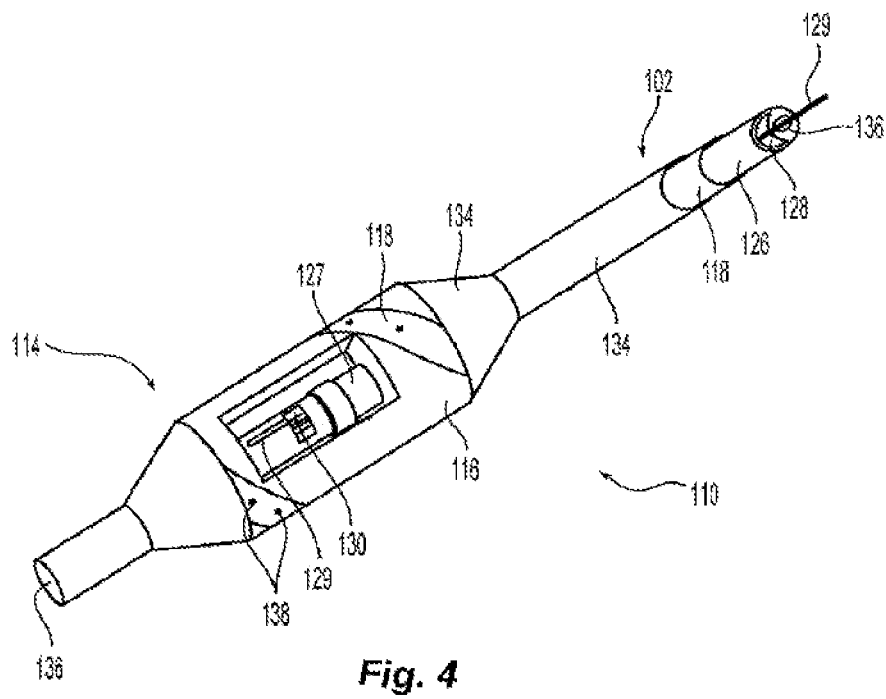
FIG. 4 shows a portion of an energy delivery device comprising a temperature sensor according to an embodiment of the present disclosure.

FIG. 4 illustrates a portion of an embodiment of a RF delivery device. Delivery device 110 is similar to the RF delivery device shown in FIGS. 1-3. Device 110 includes catheter shaft 126 covered with conductive material 118, upon which insulation material 134 is disposed. Insulation material 134 is also disposed on the proximal transition section of the expandable portion 114, similar to the embodiment shown in FIGS. 1-3. The inflatable element also has conductive material 118 disposed on the inflatable element in the form of a helical electrode. Catheter 126 has guiding element lumen 136 and irrigation lumen 128 therein. Device 110 also includes at least one marker 127 disposed on catheter 126 such that the marker is within expandable portion 114 (shown as a balloon). Device 110 also includes irrigation port 130 in fluid communication with irrigation lumen 134. Device 110 also includes temperature sensor 129, such as a thermocouple, a resistance temperature detector, or a thermistor, that is electrically coupled from the proximal end of the device (not shown) through irrigation lumen 128, out of irrigation port 130, and is secured at its distal region to catheter 126. The temperature sensor could alternatively be disposed on the inner or outer surface of inflatable element 116. In some embodiments marker 127 is a radio opaque marker comprised of Pt, PtIr, or other suitable radio opaque material. In some embodiments the marker may also comprise features viewable under fluoroscopy that allow for the visualization of the rotational orientation of the marker, and therefore the expandable section. This allows the physician to note the location of and/or realign the expandable element and helical electrode as necessary within the renal artery.

Figure 5:
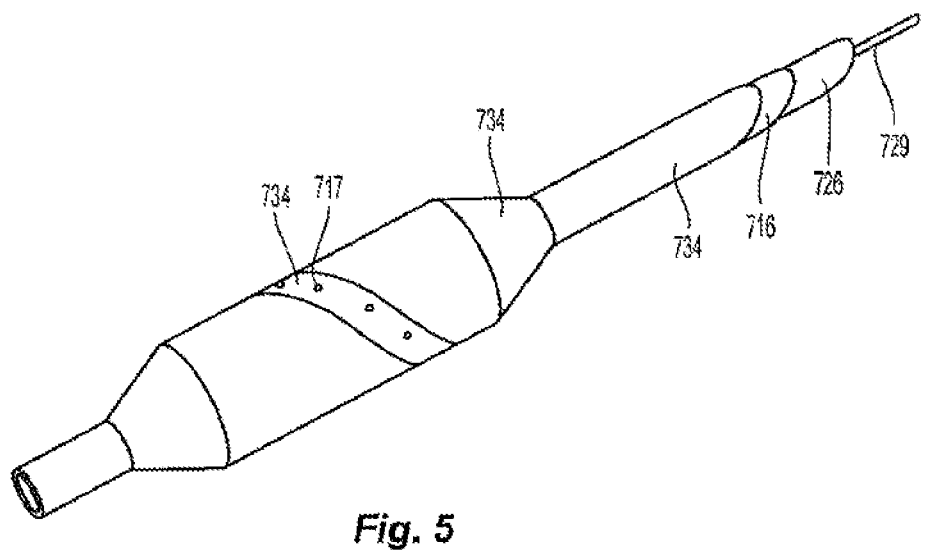
FIG. 5 illustrates a portion of an energy delivery device wherein portions of a helical electrode are covered with an insulation material according to an embodiment of the present disclosure.

The irrigation fluid is adapted to cool the electrode on the inflatable element. The irrigation fluid cools the RF electrode as it flows within the inflatable element and after it passes through the apertures as it flows across the outer surface of the inflatable element. Temperature sensor 129 is adapted to sense the temperature of the fluid within inflatable element 116. The signal from the temperature sensor may be used in a feedback control mechanism to control the flow of fluid from a fluid reservoir (now shown) into the inflatable element. Alternatively, the irrigation fluid may be delivered at a substantially constant rate and the signal from the temperature sensor used as signal to automatically shut off the RF generator if the sensed fluid temperature is above a threshold limit, thereby terminating that portion of the procedure. Such a condition is considered a fault and after identification and resolution of a fault, a procedure may be restarted. FIG. 5 illustrates a delivery device in which portions of the helical conductor have been covered by insulation material 734, forming a plurality of discrete circularly-shaped windows surrounding apertures 717 on electrical conductor 718. In this fashion a single conductor can be used to create a number of discrete burn zones following a helical path along and around a vessel wall.

Figure 6:
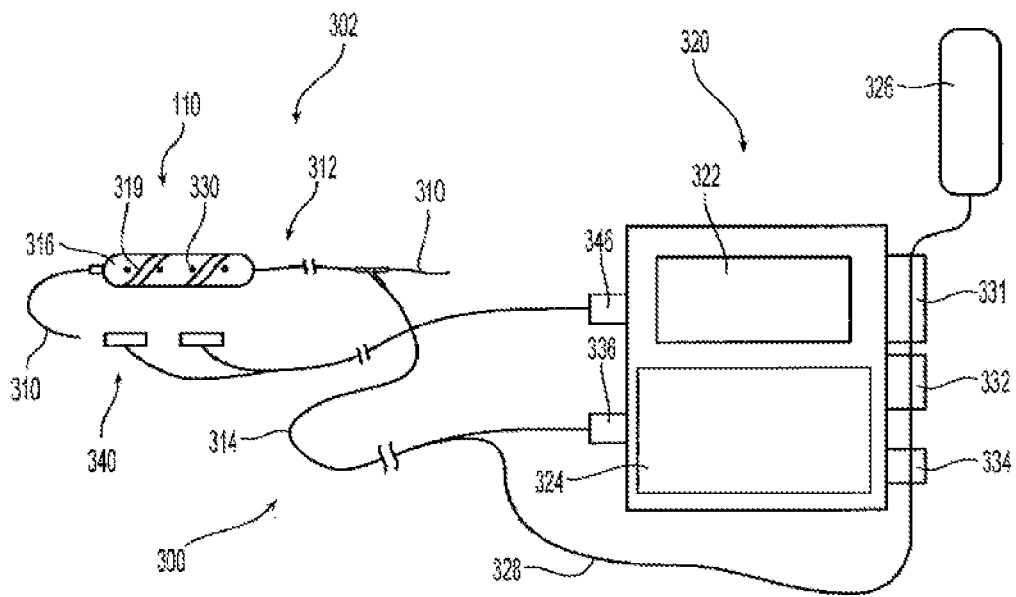
FIG. 6 illustrates an system for delivering energy to tissue according to an embodiment of the present disclosure.

One aspect of the disclosure is a system to delivery RF energy to treatment tissue. FIG. 6 illustrates a system 300 adapted to deliver RF energy to treatment tissue. System 300 includes RF energy delivery device 302, which can comprise any of the RF energy delivery devices described herein. Delivery device 302 is shown including inflatable element 316, helical energy delivery element 319, irrigation apertures 330, guidewire 310, and elongate member 312. System 300 also includes external housing 320, which includes display 322 and controller 324. Housing includes connector 336, which is adapted to connect to instrument interface cable 314. System 300 also includes fluid reservoir 326, which is in fluid communication with delivery device 302 via irrigation line 328. The system also includes fluid pump 331, optional pressure sensor 332, and optional bubble sensor 334. System 300 also includes a grounding plate or set of grounding plates 340 interfaced to controller 324 via connector 346.

Figure 14:
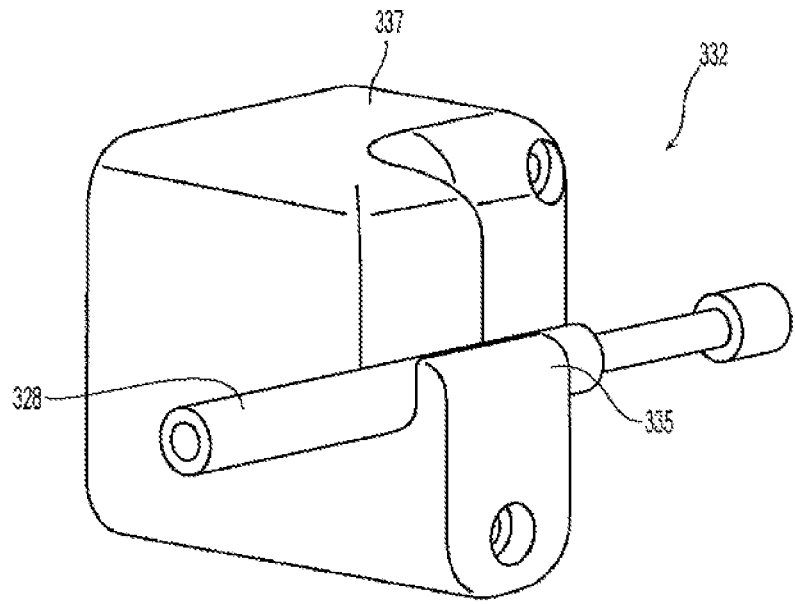
FIGS. 14 and 15 illustrate an embodiment of a pressure sensor according to an embodiment of the present disclosure.
Figure 15:
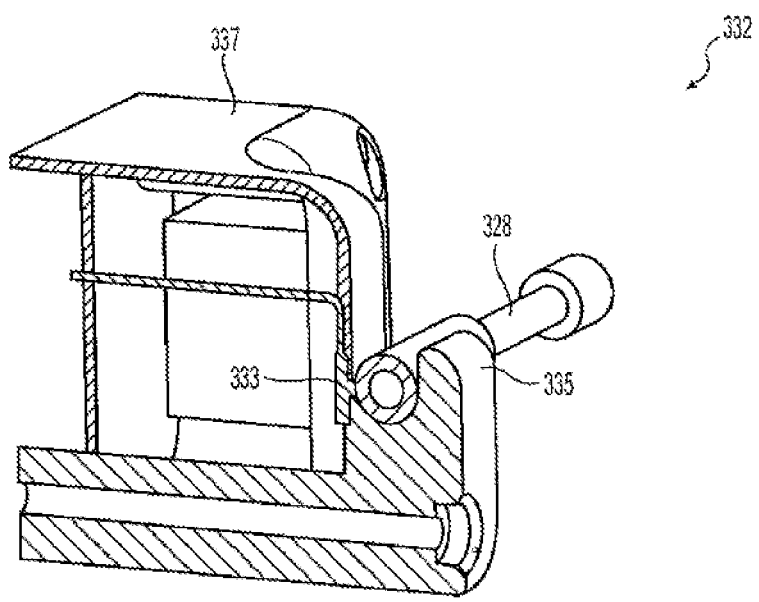

An embodiment of pressure sensor 332 from the system in FIG. 6 is shown in FIGS. 14 and 15. Pressure sensor 332 includes a housing, which comprises capture portion 335 and a force sensor 333. Capture portion 335 is configured to substantially surround irrigation tube 328. Additionally, capture portion 335 captures tubing 328 such that a portion of the wall of irrigation tube 328 is compressed against force sensor 333. The force experienced by the force sensor is then a function of the force associated by the compression of the irrigation tube and the pressure within the irrigation tube. In operation, a measurement is made under a no flow condition that describes the offset associated with the compression of the irrigation tube. This offset measurement is made prior to the initiation of a procedure and may be repeated at the beginning of each power cycle. This value is then used as an offset for subsequent measurements made under flow conditions. A force/pressure calibration per tubing type or per tube is then used to convert the force signal to a pressure value.

The disclosure includes methods of using any of the RF delivery devices and systems herein. In some embodiments the devices and/or systems are used to treat hypertension by disrupting the transmission within renal nerves adjacent one or both renal arteries.

The present methods control renal neuromodulation via thermal heating mechanisms. Many embodiments of such methods and systems may reduce renal sympathetic nerve activity. Thermally-induced neuromodulation may be achieved by heating structures associated with renal neural activity via an apparatus positioned proximate to target neural fibers. Thermally-induced neuromodulation can be achieved by applying thermal stress to neural structures through heating for influencing or altering these structures. Additionally or alternatively, the thermal neuromodulation can be due to, at least in part, alteration of vascular structures such as arteries, arterioles, capillaries, or veins that perfuse the target neural fibers or surrounding tissue.

Thermal heating mechanisms for neuromodulation include both thermal ablation and non-ablative thermal alteration or damage (e.g., via sustained heating or resistive heating). Thermal heating mechanisms may include raising the temperature of target neural fibers above a desired threshold to achieve non-ablative thermal alteration, or above a higher temperature to achieve ablative thermal alteration. For example, the target temperature can be above body temperature (e.g., approximately 37 degrees C.) but less than about 45 degrees C. for non-ablative thermal alteration, or the target temperature can be about 45 degrees C. or higher for the ablative thermal alteration.

The length of exposure to thermal stimuli may be specified to affect an extent or degree of efficacy of the thermal neuromodulation. For example, the duration of exposure can be as short as about 5, about 10, about 15, about 20, about 25, or about 30 seconds, or could be longer, such as about 1 minute, or even longer, such as about 2 minutes. In other embodiments, the exposure can be intermittent or continuous to achieve the desired result.

In some embodiments, thermally-induced renal neuromodulation may be achieved via generation and/or application of thermal energy to the target neural fibers, such as through application of a "thermal" energy field, including, electromagnetic energy, radiofrequency, ultrasound (including high-intensity focused ultrasound), microwave, light energy (including laser, infrared and near-infrared) etc., to the target neural fibers. For example, thermally-induced renal neuromodulation may be achieved via delivery of a pulsed or continuous thermal energy field to the target neural fibers. The energy field can be sufficient magnitude and/or duration to thermally induce the neuromodulation in the target fibers (e.g., to heat or thermally ablate or necrose the fibers). As described herein, additional and/or alternative methods and systems can also be used for thermally-induced renal neuromodulation.

The energy field thermally modulates the activity along neural fibers that contribute to renal function via heating. In several embodiments, the thermal modulation at least partially denervates the kidney innervated by the neural fibers via heating. This may be achieved, for example, via thermal ablation or non-ablative alteration of the target neural fibers.

In some uses in which RF energy is used to ablate the renal nerve, the RF delivery device is first positioned within one or more renal arteries and RF energy is delivered into renal nerves to disrupt the nerve transmission sufficiently to treat hypertension. The disruption pattern within the artery preferably extends substantially 360 degrees around the artery. Electrodes that treat tissue falling diametrically in a single plane normal or oblique to the longitudinal axis of the vessel have been shown to increase the risk of stenosing a vessel treated with RF energy. Spiral, or helical, patterns as described herein create patterns of treated tissue for which the projection along the longitudinal axis is circular and therefore have a high probability of treating any renal nerve passing along the periphery of the renal artery. The patterns, however, have minimal risk of creating a stenosis. Previous attempts have used a point electrode at a distal end or distal region of a device. In these attempts, the electrode is disposed in the renal artery followed by RF energy delivery. To disrupt renal nerve tissue in a non circumferential pattern using a point electrode, the device is first positioned within the renal artery adjacent arterial tissue. RF energy is then delivered to disrupt a region of renal nerve. The device must then be moved axially (distally or proximally) and rotated, followed by additional RF delivery. The movement and RF delivery is repeated in a pattern until the renal nerves have been sufficiently disrupted. The repeated movements are time consuming and increase the complexity of the overall process for the physician. During an emergency situation the physician may lose track of the position and sequence of previous burns thereby jeopardizing the likelihood of creating a pattern sufficient to treat the neural tissue or be forced to increase the number of burns thereby over-treating the patient.

Utilizing a single helical electrode as described herein provides procedural improvements over previous attempts. By using an electrode with the configuration of the desired treatment region, the device need not be moved to disrupt tissue in a desired treatment configuration. In particular the device need not be moved axially or rotated to treat an entire renal nerve treatment region. This reduces the overall time of the treatment. Additionally, this allows energy to be delivered to a desired treatment region in a variety of patients with much greater predictability. Additionally, if markers are used that allow for rotational alignment, the device may be moved and/or removed and then replaced and realigned, allowing the procedure to be restarted at a later time.

Figure 7:
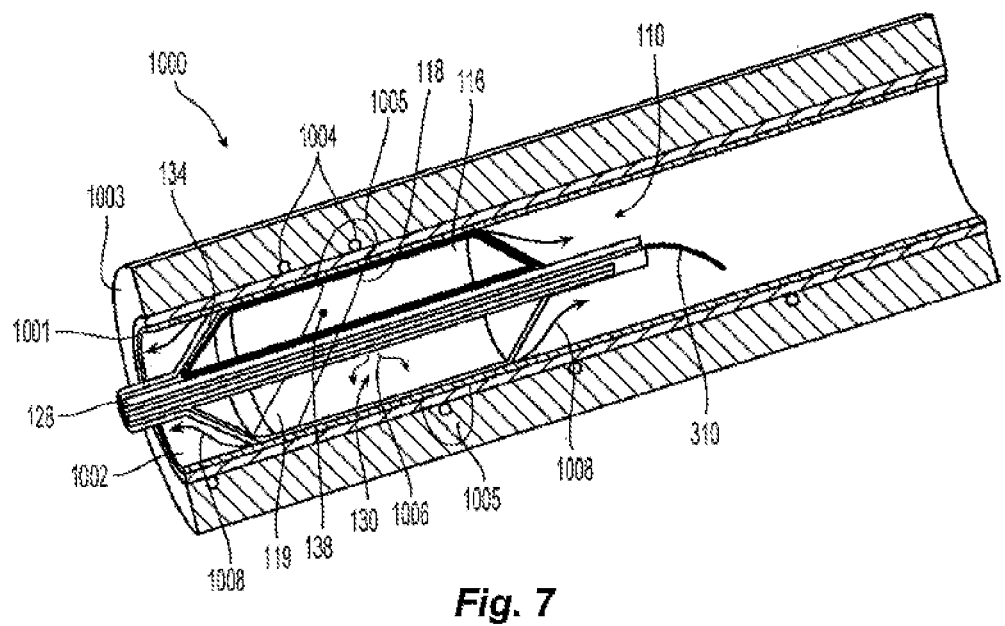
FIG. 7 illustrates a cross section of an energy delivery device with a helical electrode in use within a renal artery according to an embodiment of the present disclosure.

A method of using an RF delivery device to treat hypertension is shown in FIG. 7, and will be described using the device in FIG. 4 and the system shown in FIG. 6. The methods described herein can be carried out by other systems and by other RF delivery devices, such as the RF devices described herein.

The RF delivery device is positioned in a renal artery using a percutaneous access through a femoral artery. The expandable portion is delivered into the renal artery in a collapsed configuration (not shown). Once the expandable portion is in position, fluid from fluid reservoir 326 is pumped in an open loop control configuration, under constant flow, through irrigation line 328 and into inflatable element 116 by pump 330. Fluid flow into inflatable element 116 causes inflatable element 116 to expand. Device 110 in FIG. 7 is in a delivered, or expanded, configuration within renal artery 1000. The tunica intima 1001 is surrounded by the tunica media 1002, which is in turn surrounded by adventitial tissue 1003. Tissue renal nerves 1004 are shown within the adventitial, and some renal nerves not shown will be found within the tunica media.

The fluid continually passes through apertures 138 in the expandable portion as it is replaced with new fluid from fluid reservoir 326. Once fully expanded, the conductive material 118 on the inflatable element fully assumes the helical configuration, as shown in FIGS. 4 and 7. RE energy is then delivered to the helical electrode on the inflatable element. Control unit 324 controls the parameters of the RF alternating current being delivered through the conductive material on the catheter and the helical electrode on the inflatable element.

In general, the RF signal characteristics are chosen to apply energy to depths at which the renal nerves are disposed to effectively ablate the renal nerves. In general, the power is selected to ablate a majority of the renal nerves adjacent to where the device is positioned within the renal nerve. In some embodiments the tissue is ablated to a depth of between about 3 mm to about 7 mm from the tissue closest to the device in the renal artery.

The RF signal can have the following characteristics, but these are not intended to be limiting: the frequency is between about 400 KHz to about 500 KHz and is a sine wave; the power is between about 30 W to about 80 W, the voltage is between about 40 v and about 80 v; and the signal is an intermittent signal.

Tissue treated by the RF energy via the helical electrode comprised is shown as regions 1005, delineated by a dashed line. As illustrated, a region of treated tissue 1005 adjacent to the cut away section of conductor 118 includes nerve

1004. The device is shown being used in monopolar mode with a return electrode 340 positioned somewhere on the patient's skin.

Control unit 324 controls the operation of pump 330 and therefore controls the flow rate of the fluid from reservoir into the inflatable element. In some embodiments the pump is continuously pumping at constant flow rate such that the flow is continuous from the reservoir, as is illustrated in FIG. 7. In some embodiments the pump is operated in an open loop constant flow configuration where pump rate is not adjusted as a function of any control parameter other than an over-pressure condition sensed by pressure sensor 332, in which case RF power delivery is terminated, the pump is turned off, and an over-pressure condition reported to the operator. The pump is typically operated for a period of time which encompasses the delivery of the RF energy and turned off shortly after the conclusion of the procedure or if the pressure sensor senses an undesirable condition, discussed herein.

The irrigation fluid is delivered from the pump through irrigation line 328 to irrigation lumen 128 to irrigation port 130 into the inflatable element 116, and then out of the inflatable element through irrigation apertures 138. The pressure measured at the pressure sensor is driven by flow rate and the series sum of the fluid resistance of all of the elements in the fluid path. The choice of fluid flow rate is driven by the required cooling rate and limited by the amount of irrigant fluid that can be tolerated by the patient which is delivered during the sum of treatments cycles. The system is designed such that at the desired fluid flow there is a defined operating pressure within the inflatable element. An optimal inflatable element inflation pressure is a pressure that is sufficient to completely inflate the inflatable element such that the RF electrode engages the treatment tissue. The operating pressure within the inflatable element will be driven by the fluid flow, the number of apertures, and their cross sections. The distribution, number, and cross section of the irrigation apertures will be driven by the flow rate, the configuration of the electrode, the intended operating pressure, and the maximum desired exit velocity for the irrigation fluid. If the number of apertures is too small and the distribution too sparse some areas of the surface will not receive appropriate irrigation and thereby be subject to overheating and possible charring of tissue. For a set of circular apertures and a given flow rate, the mean exit velocity for the irrigation fluid will drop as the number of apertures is increased while decreasing the cross sectional area of each aperture such that the fluid resistance of the sum of apertures is appropriate to maintain the desired inflation pressure. Minimizing the irrigation fluid exit velocity minimizes or precludes the possibility that lesions will be eroded through the treatment tissue.

A set of operating conditions and design parameters is now provided, and is not meant to be limiting. An inflation pressure between about 0.5 atm and less than about 4 atm used with a noncompliant inflatable element of approximately 0.75 mil (~49 um) thick ensures tissue engagement in a renal artery. In some particular embodiments the inflation pressure is about 2 atm+/−0.5 atm. The irrigation fluid delivery rate is between about 1 mL/min and about 20 ml/min. In some particular embodiments the delivery rate is about 10 mL/min+/−2 mL/min. The expandable portion includes eight irrigation apertures about 2.6 mil (0.0026 inches) in diameter distributed on either side of the helical electrode and equally spaced along the edge of the electrode. In such a configuration the mean exit velocity is about 6 m/sec. In some embodiments the maximum mean fluid exit velocity is between about 1 m/see and about 20 msec.

The above operating parameters are not intended to be limiting. For example, the inflation pressure can be between about 0.5 atm (or less) and about 10 atm, the flow rate can be between about 1 mL/min to about 50 mL/min, and any suitable number of apertures with any suitable size can be incorporated into the device. Apertures may be of the same size or of different sizes and may also be uniformly or non-uniformly distributed through and/or about the electrode. The apertures are sized such that the total resistance of the set of apertures is appropriate to maintain the pressures defined herein internal to the inflatable element at the desired flows described herein. Alternatively, the total resistance is such that the desired flows described herein are maintained at the desired pressures described herein. The total resistance for the parallel combination of apertures is calculated as the inverse of the sum of the inverses of the individual aperture resistances.

The system shown also includes pressure sensor 332, which is adapted to determine if the pressure rises above or below threshold limits. If the fluid pressure rises above an established limit, the controller shuts off the RF energy, and fluid pump 330 is automatically shut off. The pressure can elevate if one or more of the apertures become blocked, preventing fluid from passing out of the balloon, which can prevent the electrode from being cooled sufficiently. Controller 324 therefore runs fluid pump 330 in a binary manner, either open-flow or off.

The system as shown also includes a temperature sensor 129 secured to the catheter within the inflatable element. If the sensed temperature of the fluid is above a threshold limit, the fluid will not properly cool the electrode. If the sensed fluid temperature is above a threshold limit, control unit 324 is adapted to cease RF current delivery. The fluid temperature in the balloon can rise if one or more apertures are blocked, preventing the electrode from being properly cooled and also increasing the risk of charring. The fluid pressure generally will rise above a threshold limit if this occurs as well. In some embodiments the system has only one of the temperature sensor and pressure sensor.

The system may also include bubble sensor 334, which is adapted to sense bubble s in the fluid line and communicates with control unit 324 to shut off pump 330 if bubbles of sufficient volume are detected.

The system can also include a flow sensor to determine if the flow rate has gone below or above threshold limits. RF energy delivery is automatically stopped and the pump is automatically shut down if the flow rate goes above or below the threshold limits.

In an alternate embodiment to that of FIG. 6 the constant flow control of the system may be replaced by constant pressure control. In such a system the reservoir 326 may be maintained at a pressure within the prescribed pressure range using, for example without limitation, an IV bag pressure cuff or other suitable means, and the pump replaced by a flow sensor or flow controller. In such a system pressure is maintained at a substantially constant level within the prescribed range and flow rate monitored. When flow rate falls outside of the proscribed range the RF power delivery is terminated.

In general, using a greater number of smaller holes provides substantially the same resistance as a fewer number of larger holes, but mean fluid exit velocity is diminished.

Figure 8:
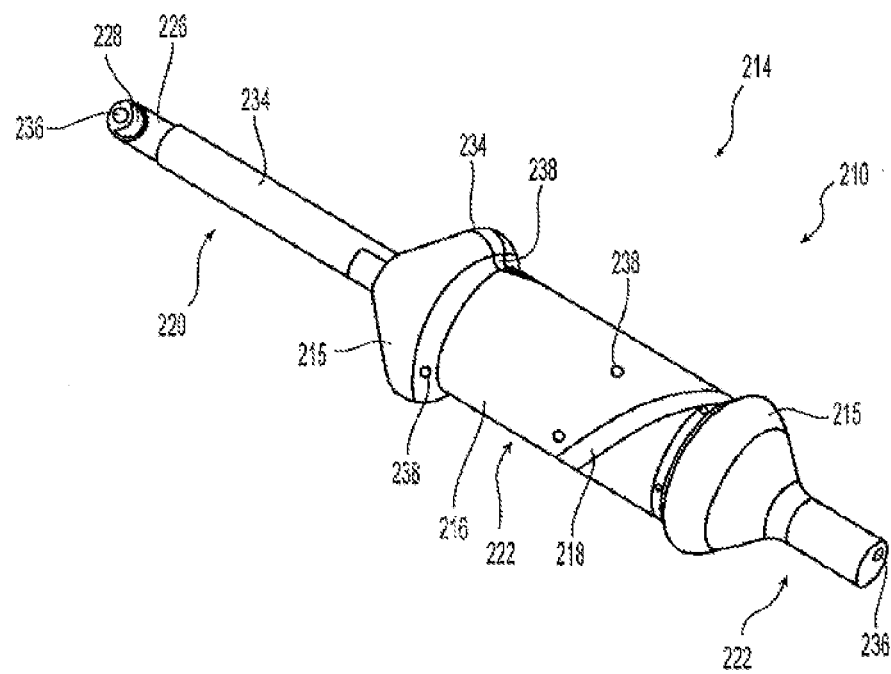
FIGS. 8 and 9 illustrate a portion of an energy delivery device wherein energy is delivered to renal nerves through conductive fluid to the tissue according to an embodiment of the present disclosure.

FIG. 8 illustrates a portion of an embodiment of an RF delivery device wherein the expandable portion has a general dumbbell configuration, and energy is delivered through the conductive fluid to the tissue. RF delivery device 210 includes expandable portion 222 that comprises inflatable element 216 on which is disposed conduction material 218 with a helical configuration. The catheter has guiding element lumen 236 and irrigation lumen 228. A conductive layer and an insulation layer are disposed on the catheter as in the embodiment in FIGS. 1-5. The proximal and distal portions of inflatable element 216 have diameters that are greater than the intermediate section, such that the expandable portion has a general dumbbell shape. When inflated, larger diameter proximal and distal ends of the expandable portion 214 contact the vessel wall, while space is left between the cylindrical section 222 of the expandable element and the vessel wall as illustrated in FIG. 8. The irrigation fluid flowing through irrigation apertures 238 fills the space between the cylindrical section 222 and tissue, and current from the helical electrode is carried through the conductive irrigation fluid and into the adjacent tissue. In this configuration the helical electrode does not contact tissue directly, therefore the uniformity of heating is improved and the risk of chaffing or overheating the tissue is reduced.

Device 210 is also adapted to query the nervous tissues adjacent to the device, but need not include this functionality. Device 210 includes nerve conduction electrodes 215 located on the outer surface of the dumbbell shaped proximal and distal ends of the expandable portion 214. In use, an electrical signal, typically a low current pulse or group of pulses is transmitted to one of the conduction electrodes. This triggers a response in adjacent renal nerves, which then travels along the nerves and at some time "t" later is sensed by the opposite electrode when the signal is traveling in the appropriate direction. By alternating which electrode is used as the exciter and which the sensor, both changes in efferent and afferent nerve conduction in the renal nerves may be monitored as a function of RE treatments induced by the RF electrode. The conduction electrodes are wired to the sensing circuits in the controller via wires traveling within the catheter shaft, as in the irrigation lumen, or additional lumens (not shown), or multiple conductors may be applied to the outer surface of the shaft (not shown).

Figure 9:
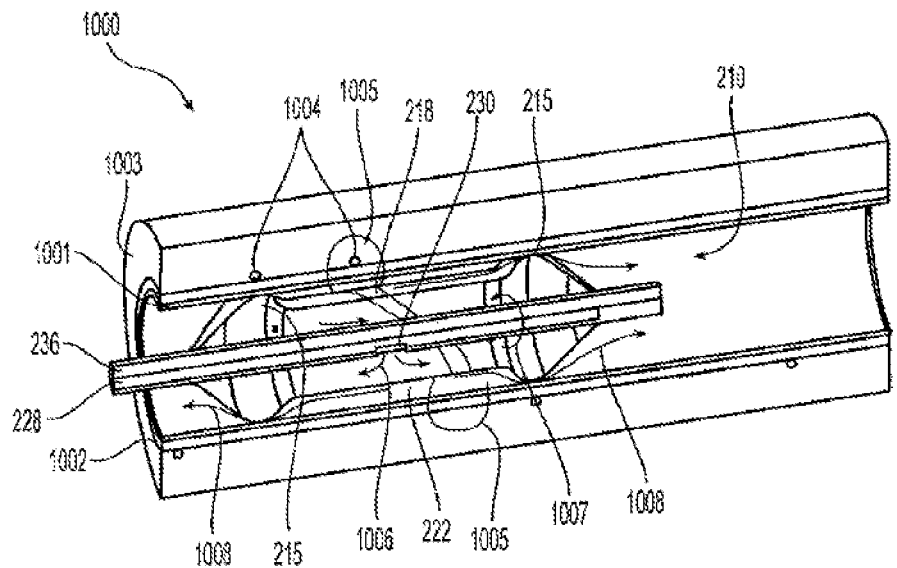

FIG. 9 illustrates the delivery device 210 in a delivered, or expanded, configuration within a renal artery. Areas 1005 indicate tissue treated by the application of RF energy delivered via the helical electrode. An area 1005 adjacent to conductor 218 surrounds a renal nerve 1004. Irrigation fluid movement is shown by the arrows. The fluid enters the inflatable element 216 at irrigation port 230 as shown by arrows 1006. The fluid then flows out of inflatable element 216 at irrigation apertures 238, shown by arrows 1007. The fluid then flows past conduction electrodes 215 into the blood stream, shown by arrows 1008.

In use, the dumbbell configuration creates a small space between the helical electrode and the arterial wall. The irrigation fluid, such as saline, can be used to act as a conductor and transfer energy from the electrode to the tissue. In such a system, the impedance variations, at the interface between the tissue and the electrode, associated with surface irregularities and variations in contact between the electrode and tissue will be minimized. In this manner the fluid can act both to cool the electrode and to transfer energy to tissue. The thin layer of fluid between the electrode and tissue can also prevent sticking and add lubrication.

Unless specifically stated to the contrary, the embodiment of FIG. 7 includes features associated with the embodiment from FIG. 4.

The configuration of RF delivery device 210 is less dependent on considerations listed above with respect to the embodiment in FIG. 4 as the irrigation fluid does not directly impinge on the treatment tissue and is allowed circulate in the space between the vessel wall and the cylindrical central section 222. Such a configuration additionally requires less irrigation fluid to prevent charring as the electrode 129 does not contact the tissue directly.

In use, the embodiment from FIG. 5 is used to create a discontinuous helical burn pattern formed of a plurality of discrete burn areas in the tissue. The helical burn pattern is formed during a single treatment session and does not require the device be moved to create the plurality of discrete burn areas.

Figure 10:
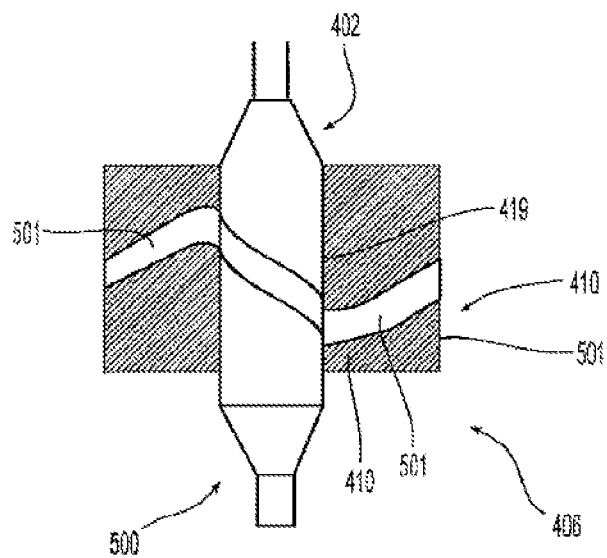
FIG. 10 is a photograph showing tissue ablation in a general helical pattern caused by an energy delivery device with a helical electrode according to an embodiment of the present disclosure.

FIG. 10 is a photograph of an RF delivery device 410 on top of a piece of heart tissue 500 which has been ablated with RF energy delivered by a device similar to that in FIG. 4 and a system similar to that of FIG. 6. The heart tissue was originally cut as a cylinder into the core of which the distal end 406 of the RF delivery device 410 was deployed. RF energy comprising a signal of 400K Hz at 40 volts and 40 watts was then delivered to the tissue. The cylinder of tissue was then cut along its length so that the inner surface of the tissue cylinder could be visualized. Helical burn zone 501 was created by helical electrode 419. The burn zone has the same configuration as the helical electrode.

Figure 11A:
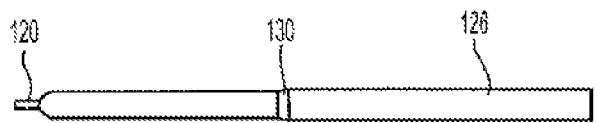
FIGS. 11A-11H illustrate a method of manufacturing an energy delivery device with a helical electrode on an expandable element according to an embodiment of the present disclosure.
Figure 11B:
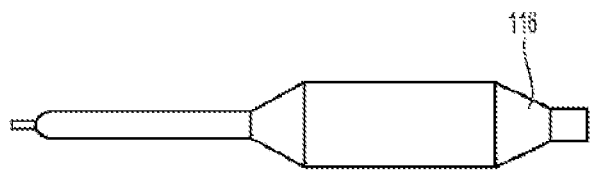

One aspect of the disclosure is a method of manufacturing RF delivery devices. FIGS. 11A-11H illustrate a method of manufacturing a portion of the RF delivery device 110 from FIG. 4. In FIG. 11A, catheter 126 is provided and can be any suitable catheter or other elongate device, such as a sheath. For example, catheter 126 can be an extruded material, and optionally can have a stiffening element therein such as a braided material. In this embodiment catheter 126 is extruded with a guide element lumen and an irrigation lumen formed therein (not shown), and the irrigation port is formed therein (not shown). The irrigation lumen is closed off at the distal end of the catheter to prevent fluid from escaping the distal end of catheter, but the irrigation lumen can stop at the irrigation port rather than continuing further towards the distal end.

Figure 11C:
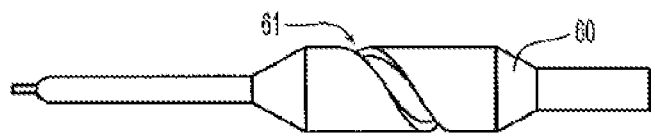
Figure 11D:
Figure 11E:
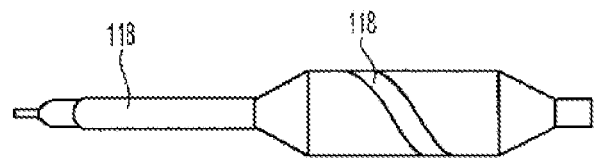
Figure 11F:
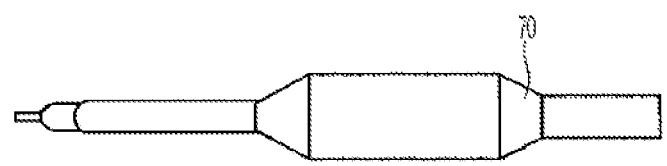
Figure 11G:
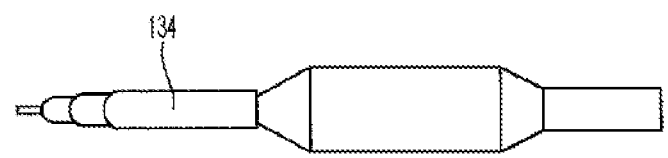
Figure 11H:
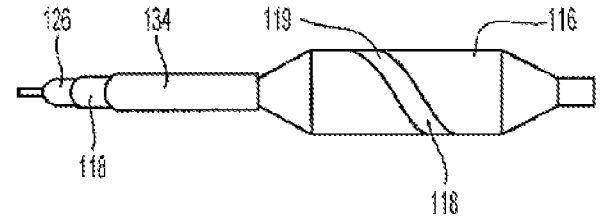

Inflatable element 116, which can be an inflatable balloon, is then secured to the exterior of catheter 126 using any suitable technique such that irrigation port 130 is disposed within inflatable element 116. Next, mask 60 is applied or slid over inflatable element 116. The mask is configured such that it covers areas where the conductive material is not to be deposited and is open where conductive material is to be applied. In FIG. 11C, mask 60 is configured with open area 61 to allow for the deposition of a conductive element 118 in a helical configuration. Inflatable element 116 is then inflated with a suitable inflation fluid (e.g., liquid or gas) delivered through the irrigation lumen and out port 130 to expand, or inflate, inflatable element 116, as shown in FIG. 11C. Additionally, mask 60 is typically configured to mask the distal transition section of the expandable portion and the catheter distal to the expandable portion. After mask 60 is applied, conductive material 118 is then deposited, in a single deposition step, onto substantially all of catheter 126, portions of inflatable element 116, and mask 60. This forms a conductive material layer on substantially all of catheter 26, proximal portion of inflatable element 116, and in the helical pattern on inflatable element 116. After the conduction material 118 is deposited in the single step and allowed to dry sufficiently and or cure, inflatable element 116 is deflated and the mask 60 is removed. As shown in FIG. 11F, a second mask 70 is then applied over those areas of conductive material 118 which are intended to deliver energy directly to the tissue in the energy delivery pattern, which is the helical pattern. The inflatable element 216 is then re-inflated and insulation material 34 is applied to substantially the entire device in a single depositing step as shown in FIG. 11G. This forms an insulation layer on substantially the entire conductive material already deposited on catheter 126, the proximal portion of the inflatable element, and the intermediate portion of the inflatable element where mask 70 is not disposed. Next, after appropriate drying and or curing the inflatable element is deflated and the mask 70 removed as shown in FIG. 11H. After mask 70 is removed, shaft 126, and proximal transition section of inflatable element is encapsulated by conductor 118 which are in turn encapsulated by dielectric 134, while helical conductive electrode 118 on the inflatable element is not covered with dielectric. The irrigation apertures are then formed, such as by laser drilling.

In some embodiments of manufacturing the device, the layers of conductive material and insulation material are between about 0.0001 and about 0.001 inches thick. In some embodiments the conductive layer is about 0.0003 inches thick. In some embodiments the insulation layer is about 0.0005 inches thick.

Alternate methods for deposition of the conductor and/or the dielectric layers which that can be used and do not require masking include ink jet and or pad printing techniques.

These methods of manufacturing form a unitary conductor. A "unitary conductor" as described herein is a single conductive material comprising both a conduction element and an electrode element wherein the conductive element communicates energy between the controller and the electrode element.

The conductive and insulation materials can each be deposited on substantially all of elongate portion 112 (excluding the portion within expandable portion 114) and expandable portion 114 in a single step, reducing the time necessary to form the conductive and insulation layers, respectively. This can also simplify the manufacturing process. To deposit the conductive and insulation material, the device can be secured to a mandrel and spun while the material is deposited, or the device can be secured in place while the device used to deposit the material is moved relative to the device, or a combination of the two steps. "Single step" as used herein includes a step that applies the material without stopping the deposition of material. For example, the conductive material can be deposited on substantially all of the catheter proximal to the inflatable element and to the inflatable element in a single step. "Single step" as used herein also includes applying a second or more coats to the elongate portion and the expandable portion after initially ceasing the deposition of material. For example, a process that applies a first coat of conductive material to substantially all of the catheter proximal to the inflatable element and to the inflatable element, followed by a ceasing of the deposition, but followed by application of a second coat to substantially the entire portion of the catheter proximal to the inflatable element and to the inflatable element, would be considered a "single step" as used herein. Some previous attempts to form a conductive material on an elongate device formed one or more discrete conductive elements on the elongate device, thus complicating the deposition process. These and other attempts failed to appreciate being able to form a single layer of conductive material on substantially all of the catheter or other elongate device. These attempts failed to appreciate being able to form single layer of conductive material on the catheter and an electrode element on an expandable element in a single step.

By disposing the conductive material on the external surfaces of the catheter and inflatable element in a single step, the creation of electrical junctions is avoided. For example, a junction need not be formed between the conductive material on the catheter and the conductive material on the inflatable element. As used herein, electrical junction refers to a connection created between two conductive materials, either the same or different materials, that allows an electrical signal to be conducted from one material to the other.

The inflatable element is, in some embodiments, an inflatable balloon that is adapted to be inflated upon the delivery of a fluid through the irrigation lumen and out of the irrigation port. In the embodiment in FIGS. 1-11, the inflatable element is a balloon made of non-elastic, or non-compliant, material, but it can be a compliant, or elastic, material as well. Materials for a non-compliant balloon include, without limitation, polyethylene, polyethylene terephthalate, polypropylene, cross-linked polyethylene, polyurethane, and polyimide. Materials for a compliant balloon include, without limitation, nylon, silicon, latex, and polyurethane.

In some embodiments of the embodiment in FIG. 4, the length of the cylindrical intermediate portion of the inflatable element is between about 1 cm and about 4 cm. In some embodiments the inflatable element has a diameter between about 4 mm and about 10 mm. In some particular embodiments the length of the intermediate portion of the inflatable element is about 20 mm and the diameter is about 5 mm to about 7 mm.

The conductive material can be deposited onto the catheter and/or expandable portion. Methods of depositing include, without limitation, pad printing, screen printing, spraying, ink jet, vapor deposition, ion beam assisted deposition, electroplating, electroless plating, or other printed circuit manufacturing processes.

In some embodiments the conductive material deposited is an elastomeric ink and the dielectric material is an elastomeric ink. They can be sprayed on the respective components. In some embodiments the elastomeric ink is diluted with an appropriate diluent to an appropriate viscosity then sprayed in a number of coats while the delivery device is rotated beneath a linearly translating spray head.

Conductive materials that can be deposited on the device to form one or more conductive layers of the device include conductive inks (e.g., electrically conductive silver ink, electrically conductive carbon ink, an electrical conductive gold ink), conductive powders, conductive pastes, conductive epoxies, conductive adhesives, conductive polymers or polymeric materials such as elastomers, or other conductive materials.

In some embodiments the conductive material comprises an elastomeric matrix filled with conductive particles. Elastomeric components include silicones and polyurethanes. Conductive materials are conductive metals such as gold or silver. Conductive inks that can be used are conductive ink CI-1065 and CI-1036 manufactured by ECM of Delaware Ohio. This ink is an extremely abrasion resistant, flexible, and highly conductive elastomeric ink. The ink has the following properties: 65% solids in the form of silver flakes; 0.015 ohms/square (1 mil (0.001 inches) thick); and a 10 minute cure time at 248 F.

The electrodes described herein can also be used as a temperature sensor. Ablative electrodes are routinely used in wide variety of surgical procedures. Many of these procedures are performed percutaneously, and a subset are performed endovascularly. In many of these procedures it is customary to incorporate provisions to monitor the temperature of the ablative electrodes. This temperature information is then used in some fashion as an input in a control scheme to limit the maximum temperature the electrode is allowed to attain. In this fashion a number of mechanisms, that may be deleterious to the desired outcome, may be controlled and or limited. Some of these effects, which in some circumstances are considered deleterious are, tissue charring, creation of steam, and the resultant uncontrolled, rapid, or large changes in interface impedance.

The temperature monitoring is typically carried out by incorporating and mounting some form of a temperature sensor such as a thermocouple, an rdt, or a thermistor in proximity to, or on, the electrode.

The electrodes are typically comprised of metals or metal alloys which are either deposited as metals directly through various metal deposition procedures such as, but not limited to physical or chemical metal vapor deposition, or applied as a component in a matrix such as but not limited to organic polymers in the form of an ink. Such inks are deposited in many ways, a few of which are, screening, spraying, ink jetting.

Metals, metal alloys, and other metal compound have resistance characteristics which are dependent on temperature, typically called the temperature coefficient of resistance or "tempco." The magnitude and characteristics of these effects varies and is often used in devices such as a resistance temperature detector "RTD", such as a platinum rtd's, or in positive temperature coefficient "PTC" or negative temperature coefficient "NTC" thermistors.

The systems herein can therefore alternatively monitor temperature by using the inherent tempco of the electrode itself as a way of monitoring its temperature and or controlling its impedance and thereby self-limiting its power output and thereby its temperature.

Figure 12:
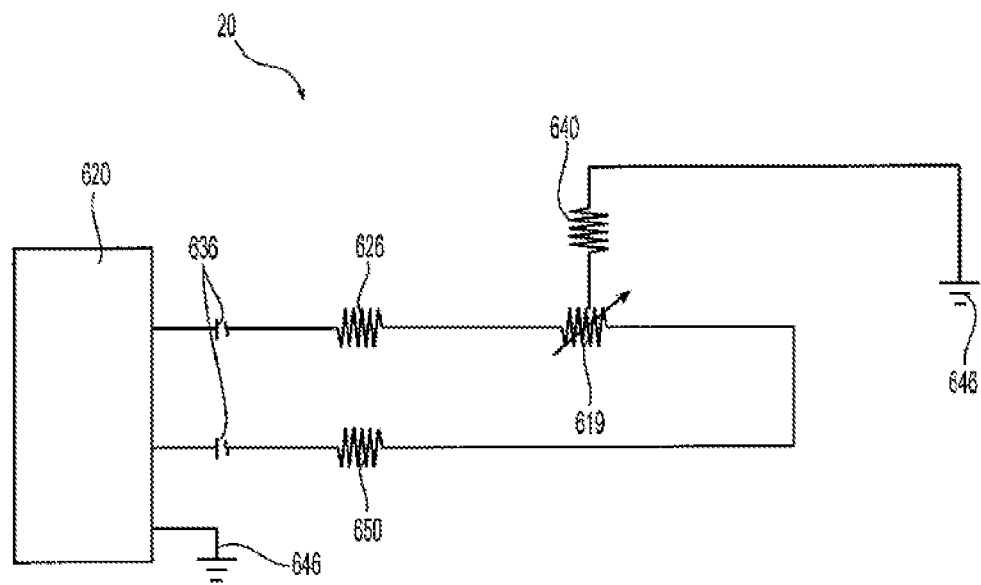
FIG. 12 represents an embodiment of a system similar to that of FIG. 6 represented by the resistances of the various elements according to an embodiment of the present disclosure.

FIG. 12 represents an embodiment of a system similar to that of FIG. 6 represented by the resistances of the various elements. The delivery RF lead which runs down catheter is represented as resistance 626 and the electrode is represented by resistance 619. In this embodiment there is an additional conductive element miming along the catheter shaft which is a return line represented by resistance 650. In use the leads whose resistances are represented by 626 and 650 may be sourced in parallel when RF is delivered to electrode 619 and addressed separately when used to characterize the resistance and hence temperature of the electrode 619. Alternatively one of them may be used solely for the purpose of monitoring temperature and therefore left open circuited when RF is being delivered. The design of the delivery system and electrode will be such that the impedance 640 of the patient will be orders of magnitude greater then the impedances for the delivery leads 626, 650, and the electrode 619. In one embodiment impedance 619 will be considerably greater than 626 or 650, or in some cases the parallel combination of 626 and 650.

In one embodiment the electrode is comprised of a layer of platinum and the temperature of the electrode may be characterized by monitoring the voltage drop across the series resistances 626, 619, 650. This may be done intermittently, interspersed in the delivery of the RF energy. As the electrode heats, its resistance will increase in a well-known and repeatable fashion. As the leads 626 and 650 have lower resistance and will not self-heat appreciable, the change in resistance will by primarily due to the heating of electrode 619 and variation in its resistance. Many other scenarios will be understood to those skilled in the art.

An alternate arrangement which relies on the use of a PTC for the electrode relies on the rapid change in resistance of the electrode past a particular set point which is a function of the composition of the electrode. In this configuration the tempco of the electrode is relatively small, for example, below about 40 C but above about 40 C. In this temperature range the tempco rapidly increases thereby limiting delivered power in a voltage-limited RF configuration. Many alternate embodiments will be understood by those skilled in the art.

Figure 13:
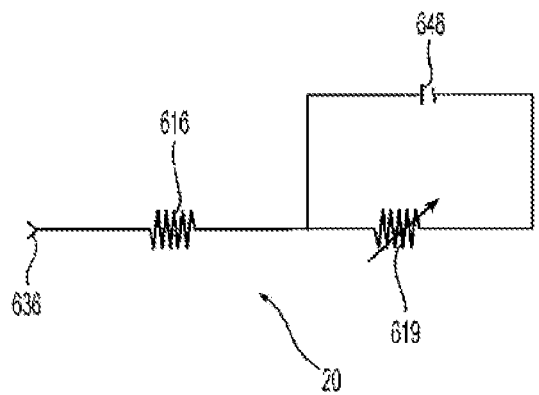
FIG. 13 illustrates an alternative configuration in which a capacitor, inductor, or both may be incorporated in the circuit from FIG. 12.

FIG. 13 illustrates an alternative configuration in which a capacitor 648, inductor (not shown), or both may be incorporated in the circuit. In one embodiment the circuit may incorporate only one source lead 621 and the inherent resonance of the circuit which will depend on the varying impedance of the electrode resistance 623.

In yet another alternative the tempco associated with a conductive ink such as the ECM CI-1036 may be used. Experimentally the ECM CI-1036 demonstrated a 0.1% increase in impedance per degree over the range of 30 C to 60 C.

Figure 16:
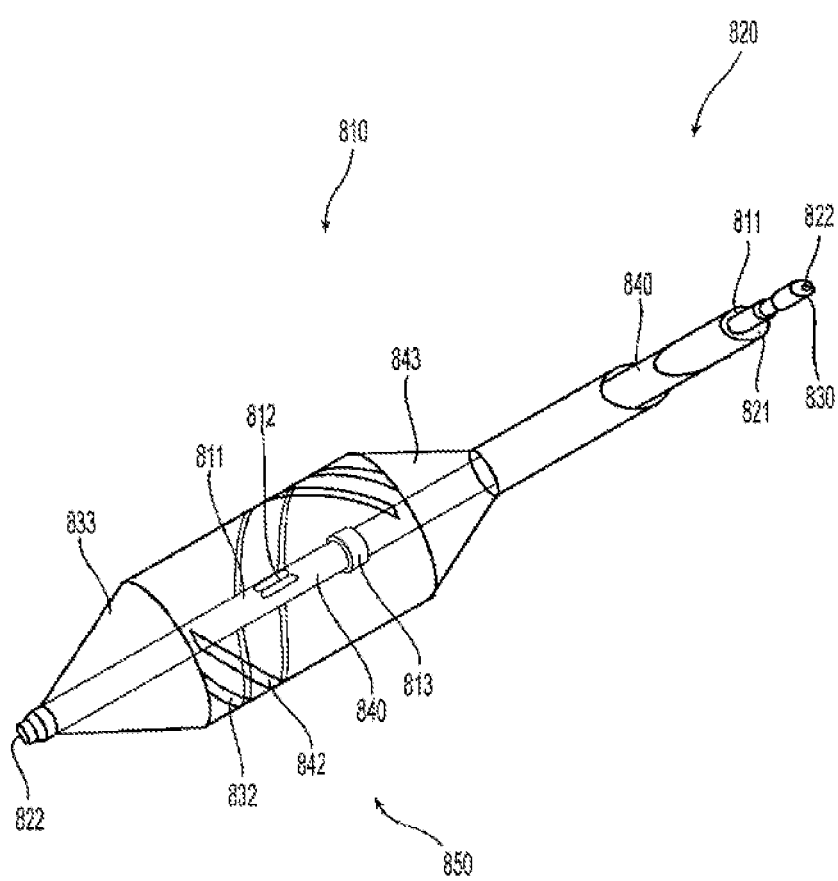
FIG. 16 illustrates a portion of an energy delivery device including a helical electrode pair on an expandable element according to another embodiment of the present disclosure.

As described above, devices capable of ablating renal nerves surrounding the renal arteries are useful in treating hypertension. The device disclosed in FIG. 16 is another embodiment of a device adapted for such purpose. The device described herein comprises a bipolar electrode pair disposed on the outer surface of an expandable structure comprised of an inflatable balloon. A bipolar electrode pair provides for both a more controlled burn and a shallower burn than a comparable monopolar electrode. The device is configured for endovascular delivery to a renal artery. Each of the individual electrodes comprising the bipolar set is in turn comprised of a unitary electrode/conductor.

Referring to FIG. 16, detailed description of the distal features of an embodiment of the device is as follows. The distal portion of an bipolar RF delivery device 810 includes an expandable section 850 including a balloon, and a catheter shaft section 820 including an inner shaft 830 and an outer shaft 840. The inner lumen of the inner shaft 830 includes a guidewire lumen 822. The annular gap between the inner and outer shafts includes an irrigation lumen 821. The outer shaft 840 also includes an irrigation outflow 812 (e.g., an irrigation port) located near its distal end such that it is disposed within the balloon. A temperature sensor 811 may be located within the balloon 850 and interconnecting leads of the temperature sensor 811 may be routed through the irrigation lumen outflow 812 and irrigation lumen 821.

Prior to assembly, a conductive material is deposited on substantially the entire inner shaft 830. A dielectric material is then deposited on the conductive material except at the distal most end of the inner shaft 830. The inner shaft 830 is then fitted within the outer shaft 840 and the two are affixed to one another such that the inner shaft 830 extends beyond the most distal portion of the outer shaft 840 and the balloon 850. The dielectric on the inner shaft 830 is deposited on at least the portions of the surface of the conductor on the inner shaft 830 that would contact irrigation fluid, thus preventing the conductive material on the inner shaft 830 from coming into contact with irrigation fluid. The distal end of the inner shaft 830, which extends distal to the outer shaft 840, is not coated with dielectric. This allows the inner shaft 830 to be in electrical communication with the inner sourced electrode as described below.

Next, the outer shaft 840 and balloon 850 are coated with an elastomeric ink, and then, subsequently, by a dielectric as described above. The conductive coating is deposited on the outer shaft 840, all or a portion of the proximal cone 843 of the balloon 850, and on the balloon 850, forming a conductive material that includes an outer sourced spiral electrode 842. This conductive material can be deposited in a unitary manner, as is described above and in the materials incorporated by reference herein. Conductive material is also deposited on the most distal section of the shaft assembly, the distal cone portion 833 of the balloon 850, and the balloon 850, forming a conductive material that includes an inner sourced electrode 832. This conductor can also be formed in a unitary manner. The conductive material that forms the inner sourced electrode cart be the same material that is used for the outer sourced electrode. When the distal conductor (which includes the inner sourced electrode 832) is formed, it interfaces electrically with the conductor on the inner shaft 830 that extends distal to the balloon 850. The conductive materials can be selected such that when the conductive materials are deposited, the interface is a single layer of the same material rather than two distinct layers. The conductor and dielectric structures can be fabricated as described above. When used in bipolar mode, energy passes from one spiral electrode 832 or 842, through renal nerve tissue, to the other electrode. The electrodes 832, 842 can be used in a bipolar manner, or each electrode can be used in monopolar mode. Bipolar mode can be used if the tissue burn need not be as deep as may be needed if using a monopolar mode. Bipolar mode generally allows more control in the tissue burn. Additionally or alternatively, the electrodes 832, 842 can be used together as a single monopolar electrode (e.g., by feeding both electrodes with the same frequency and RF energy such that the electrodes appear to be one electrode).

In an alternative embodiment, the inner shaft is not coated with a conductor (or dielectric) and, instead, a wire extends through the irrigation lumen, and interfaces the conductor that includes the inner sourced electrode.

Although not shown in FIG. 16, irrigation ports as described above can be situated such that they pass through the electrode structures, sit adjacent to the electrode structures such as in the space between them or exterior to the pair, or both.

One or more radio opaque markers 813 may be affixed to the outer shaft.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. An expandable energy delivery assembly adapted to deliver energy to tissue, the assembly comprising:
    an elongate device comprising a wall defining an irrigation lumen therethrough and an irrigation port extending across a thickness of the wall, the irrigation port being proximal to a distal end of the elongate device;
    an inflatable element secured to the elongate device such that the irrigation port is disposed within a fluid chamber defined by the inflatable element;
    an electrode disposed on the inflatable element,
    wherein the inflatable element defines at least one irrigation aperture in fluid communication with the irrigation port and adapted to allow cooling fluid to pass from within the fluid chamber to outside the inflatable element, and
    wherein the at least one irrigation aperture is sized to maintain a pressure of the cooling fluid within the inflatable element between about 0.5 atm and about 4 atm when a substantially constant irrigation flow rate of the cooling fluid from a fluid source into the inflatable element is between about 5 mL/min and about 15 mL/min.

2. The assembly of claim 1 further comprising a temperature sensor adapted to measure a fluid temperature of the cooling fluid, the assembly further comprising an energy source and a controller, the controller adapted to automatically turn off the energy source in response to determining a sensed fluid temperature is above a threshold limit.

3. The assembly of claim 2 wherein the temperature sensor is disposed within the inflatable element.

4. The assembly of claim 1 wherein the assembly comprises a flow rate sensor adapted to sense a fluid flow rate of the cooling fluid, the assembly further comprising an energy source and a controller, the controller adapted to automatically turn off the energy source in response to determining a sensed flow rate falls below a minimum value.

5. The assembly of claim 1 wherein the assembly comprises a pressure sensor adapted to sense a fluid pressure of the cooling fluid in the fluid chamber, the assembly further comprising an energy source and a controller, the controller adapted to automatically turn off the energy source in response to determining a sensed pressure falls below a minimum value.

6. The assembly of claim 1, wherein the irrigation port is between proximal and distal ends of the fluid chamber.

7. The assembly of claim 1, wherein the irrigation port is distal to a proximal end of the fluid chamber.

8. A method of providing an irrigation cooling fluid to an inflatable medical device, the method comprising:
    continuously flowing a cooling fluid at a substantially constant flow rate between about 5 mL/min and about 15 mL/min from a fluid source and into an irrigation lumen of an elongate device, the elongate device comprising a wall defining an irrigation port extending across a thickness of the wall or at a distal end of the elongate device, while allowing the cooling fluid to flow out of a fluid chamber defined by an inflatable element secured to the elongate device through at least one irrigation aperture defined by the inflatable element, the irrigation lumen being in fluid communication with the fluid chamber, the at least one irrigation aperture being in fluid communication with the irrigation port; and
    maintaining a fluid pressure of the cooling fluid within the inflatable element between about 0.5 atm and about 4 atm while continuously flowing the cooling fluid at the substantially constant flow rate between about between about 5 mL/min and about 15 mL/min.

9. The method of claim 8 further comprising delivering RF energy to tissue via an energy element disposed on the inflatable element.

10. The method of claim 9 further comprising stopping the delivery of RF energy in response to determining a fluid pressure of the cooling fluid within the inflatable element falls outside of a control range.

11. The method of claim 10 further comprising stopping the delivery of RF energy in response to determining a flow rate through the inflatable element falls outside of a control range.

12. The method of claim 8 further comprising sensing a temperature of the cooling fluid.

13. The method of claim 12 further comprising stopping the delivery of RF energy if the sensed temperature is above a threshold temperature.

14. The method of claim 8 further comprising delivering RF energy through a unitary conductor comprising an electrode.

15. The method of claim 14 wherein the delivering step comprises delivering RF energy through a helically-configured electrode.

16. The method of claim 8 further comprising;
endovascularly disposing the inflatable element in a renal artery; and
applying RF energy through an electrode on the inflatable element to renal nerves to disrupt transmission of neural signals along the renal nerves to treat hypertension.

17. A method of providing an irrigation cooling fluid to an inflatable medical device, the method comprising:
introducing cooling fluid into an irrigation lumen of an elongate device comprising a wall defining an irrigation port extending across a thickness of the wall or at a distal end of the elongate device, an inflatable element being secured to the elongate device, and the inflatable element defining a fluid chamber and defining at least one irrigation aperture therein, wherein the irrigation lumen is in fluid communication with the fluid chamber; and
maintaining a substantially constant pressure of the cooling fluid between about 0.5 atm and about 4 aim within the inflatable element sufficient to maintain a flow rate of the cooling fluid of between about 5 mL/min and about 15 mL/min through the inflatable element and out of the at least one irrigation aperture.

18. The method of claim 17 further comprising delivering RF energy to tissue via an energy element disposed on the inflatable element.

19. The method of claim 18 further comprising stopping the delivery of RF energy in response to determining a pressure within the inflatable element falls outside of a control range.

20. The method of claim 18 further comprising stopping the delivery of RF energy in response to determining a flow rate of the cooling fluid through the inflatable element falls outside of a control range.

21. The method of claim 17 further comprising sensing a temperature of the cooling fluid.

22. The method of claim 21 further comprising stopping the delivery of RF energy in response to determining the sensed temperature is above a threshold temperature.

23. The method of claim 17 further comprising delivering RF energy through a unitary conductor comprising an electrode.

24. The method of claim 23 wherein the delivering step comprises delivering RF energy through a helically-configured electrode.

25. The method of claim 17 further comprising:
endovascularly disposing the inflatable element in a renal artery; and
applying RF energy through an electrode on the inflatable element to renal nerves to disrupt transmission of neural signals along the renal nerves to treat hypertension.

* * * * *